(12) United States Patent
O'Malley

(10) Patent No.: US 11,974,764 B2
(45) Date of Patent: May 7, 2024

(54) SELF-ORIENTING ROTATING STENTRIEVER PINCHING CELLS

(71) Applicant: Neuravi Limited, Galway (IE)

(72) Inventor: Thomas O'Malley, Westport (IE)

(73) Assignee: NEURAVI LIMITED, Galway (IE)

(*) Notice: Subject to any disclaimer, the term of this patent is extended or adjusted under 35 U.S.C. 154(b) by 107 days.

(21) Appl. No.: 17/338,830

(22) Filed: Jun. 4, 2021

(65) Prior Publication Data
US 2022/0387055 A1 Dec. 8, 2022

(51) Int. Cl.
*A61B 17/221* (2006.01)
*A61B 17/22* (2006.01)

(52) U.S. Cl.
CPC ........... *A61B 17/22031* (2013.01); *A61B 2017/22034* (2013.01); *A61B 2017/22035* (2013.01); *A61B 17/221* (2013.01)

(58) Field of Classification Search
CPC .......... A61B 17/22031; A61B 17/22; A61B 2017/22035; A61B 2017/22034; A61B 17/221; A61B 2017/2212; A61B 2017/2215; A61B 17/32056; A61B 17/22012; A61B 2017/922; A61B 17/22004; A61B 2017/22004; A61B 2017/22031
See application file for complete search history.

(56) References Cited

U.S. PATENT DOCUMENTS

| 4,397,145 A * | 8/1983 | Reist ................ F16G 13/10 74/89.21 |
| 4,455,717 A | 6/1984 | Gray |
| 4,511,073 A * | 4/1985 | Furutsu ................ B65C 7/005 227/67 |

(Continued)

FOREIGN PATENT DOCUMENTS

| CN | 2557083 Y | 6/2003 |
| CN | 101172051 A | 5/2008 |

(Continued)

OTHER PUBLICATIONS

US 6,348,062 B1, 02/2002, Hopkins et al. (withdrawn)

(Continued)

*Primary Examiner* — Shaun L David
*Assistant Examiner* — Mitchell Brian Hoag
(74) *Attorney, Agent, or Firm* — TROUTMAN PEPPER HAMILTON SANDERS LLP

(57) ABSTRACT

A clot removal device for removing a clot from a body vessel, the clot removal device including: an elongated member sized to traverse vasculature and having a proximal end and a distal end, the elongated member comprising a longitudinal axis; and an engagement structure connected to the distal end of the elongated member, the engagement structure comprising a plurality of pinching cells connected to each other, the at least one pinching cell being configured to engage clot in an expanded deployed configuration and to pinch the clot upon actuation to the clot pinching configu- (Continued)

ration, a first pinching cell of the plurality of pinching cells being connected to a second pinching cell of the plurality of pinching cells such that the second pinching cell is rotatable respective the first pinching cell substantially about the longitudinal axis.

19 Claims, 8 Drawing Sheets

(56) References Cited

U.S. PATENT DOCUMENTS

| | | | |
|---|---|---|---|
| 4,542,838 A * | 9/1985 | Perez-Tubens | A47G 25/16 223/87 |
| 4,611,594 A | 9/1986 | Grayhack et al. | |
| 4,612,931 A | 9/1986 | Dormia | |
| 4,643,184 A | 2/1987 | Mobin-Uddin | |
| 4,727,873 A | 3/1988 | Mobin-Uddin | |
| 4,793,348 A | 12/1988 | Palmaz | |
| 4,873,978 A | 10/1989 | Ginsburg | |
| 5,011,488 A | 4/1991 | Ginsburg | |
| 5,084,065 A | 1/1992 | David et al. | |
| 5,092,839 A | 3/1992 | Kipperman | |
| 5,100,423 A | 3/1992 | Fearnot | |
| 5,102,415 A | 4/1992 | Guenther et al. | |
| 5,108,419 A | 4/1992 | Reger et al. | |
| 5,122,136 A | 6/1992 | Guglielmi et al. | |
| 5,163,951 A | 11/1992 | Pinchuk et al. | |
| 5,171,233 A | 12/1992 | Amplatz et al. | |
| 5,171,259 A | 12/1992 | Inoue | |
| 5,217,441 A | 6/1993 | Shichman | |
| 5,234,437 A | 8/1993 | Sepetka | |
| 5,236,447 A | 8/1993 | Kubo et al. | |
| 5,330,482 A | 7/1994 | Gibbs et al. | |
| 5,383,887 A | 1/1995 | Nadal | |
| 5,387,219 A | 2/1995 | Rappe | |
| 5,387,226 A | 2/1995 | Miraki | |
| 5,411,156 A * | 5/1995 | Reckamp | B65D 51/26 215/296 |
| 5,449,372 A | 9/1995 | Schmaltz et al. | |
| 5,499,985 A | 3/1996 | Hein et al. | |
| 5,538,512 A | 7/1996 | Zenzon et al. | |
| 5,538,515 A | 7/1996 | Kafry et al. | |
| 5,549,626 A | 8/1996 | Miller et al. | |
| 5,558,652 A | 9/1996 | Henke | |
| 5,609,627 A | 3/1997 | Goicoechea et al. | |
| 5,624,461 A | 4/1997 | Mariant | |
| 5,639,277 A | 6/1997 | Mariant et al. | |
| 5,639,278 A | 6/1997 | Dereume et al. | |
| 5,645,558 A | 7/1997 | Horton | |
| 5,653,605 A | 8/1997 | Woehl et al. | |
| 5,658,296 A | 8/1997 | Bates et al. | |
| 5,665,117 A | 9/1997 | Rhodes | |
| 5,695,519 A | 12/1997 | Summers et al. | |
| 5,709,704 A | 1/1998 | Nott et al. | |
| 5,713,853 A | 2/1998 | Clark et al. | |
| 5,733,325 A | 3/1998 | Robinson et al. | |
| 5,769,871 A | 6/1998 | Mers Kelly et al. | |
| 5,769,884 A | 6/1998 | Solovay | |
| 5,779,686 A | 7/1998 | Sato et al. | |
| 5,779,716 A | 7/1998 | Cano et al. | |
| 5,800,519 A | 9/1998 | Sandock | |
| 5,810,874 A | 9/1998 | Lefebvre | |
| 5,814,064 A | 9/1998 | Daniel et al. | |
| 5,824,041 A | 10/1998 | Lenker et al. | |
| 5,827,304 A | 10/1998 | Hart | |
| 5,853,422 A | 12/1998 | Huebsch et al. | |
| 5,855,598 A | 1/1999 | Pinchuk | |
| 5,893,869 A | 4/1999 | Barnhart et al. | |
| 5,895,398 A | 4/1999 | Wensel et al. | |
| 5,897,567 A | 4/1999 | Ressemann et al. | |
| 5,904,698 A | 5/1999 | Thomas et al. | |
| 5,911,702 A | 6/1999 | Romley et al. | |
| 5,911,725 A | 6/1999 | Boury | |
| 5,919,126 A | 7/1999 | Armini | |
| 5,931,509 A | 8/1999 | Bartholomew | |
| 5,935,139 A | 8/1999 | Bates | |
| 5,947,995 A | 9/1999 | Samuels | |
| 6,063,113 A | 5/2000 | Kavteladze et al. | |
| 6,066,149 A | 5/2000 | Samson et al. | |
| 6,066,158 A | 5/2000 | Engelson et al. | |
| 6,093,196 A | 7/2000 | Okada | |
| 6,093,199 A | 7/2000 | Brown et al. | |
| 6,096,053 A | 8/2000 | Bates | |
| 6,099,534 A | 8/2000 | Bates et al. | |
| 6,099,559 A | 8/2000 | Nolting | |
| 6,102,932 A | 8/2000 | Kurz | |
| 6,106,548 A | 8/2000 | Roubin et al. | |
| 6,129,739 A | 10/2000 | Khosravi | |
| 6,143,022 A | 11/2000 | Shull et al. | |
| 6,146,404 A | 11/2000 | Kim et al. | |
| 6,156,064 A | 12/2000 | Chouinard | |
| 6,165,194 A | 12/2000 | Denardo | |
| 6,165,199 A | 12/2000 | Barbut | |
| 6,168,604 B1 | 1/2001 | Cano | |
| 6,168,622 B1 | 1/2001 | Mazzocchi | |
| 6,174,318 B1 | 1/2001 | Bates et al. | |
| 6,179,861 B1 | 1/2001 | Khosravi et al. | |
| 6,203,561 B1 | 3/2001 | Ramee et al. | |
| 6,214,026 B1 | 4/2001 | Lepak et al. | |
| 6,221,006 B1 | 4/2001 | Dubrul et al. | |
| 6,221,096 B1 | 4/2001 | Aiba et al. | |
| 6,231,597 B1 | 5/2001 | Deem et al. | |
| 6,238,412 B1 | 5/2001 | Dubrul et al. | |
| 6,245,012 B1 | 6/2001 | Kleshinski | |
| 6,245,087 B1 | 6/2001 | Addis | |
| 6,251,122 B1 | 6/2001 | Tsukernik | |
| 6,254,571 B1 | 7/2001 | Hart | |
| 6,264,663 B1 | 7/2001 | Cano | |
| 6,267,777 B1 | 7/2001 | Bosma et al. | |
| 6,290,710 B1 | 9/2001 | Cryer et al. | |
| 6,312,444 B1 | 11/2001 | Barbut | |
| 6,315,778 B1 | 11/2001 | Gambale et al. | |
| 6,325,815 B1 | 12/2001 | Kusleika et al. | |
| 6,325,819 B1 | 12/2001 | Pavcnik et al. | |
| 6,334,864 B1 | 1/2002 | Amplatz et al. | |
| 6,336,934 B1 | 1/2002 | Gilson et al. | |
| 6,346,116 B1 | 2/2002 | Brooks et al. | |
| 6,348,056 B1 | 2/2002 | Bates et al. | |
| 6,350,271 B1 | 2/2002 | Kurz et al. | |
| 6,355,057 B1 | 3/2002 | DeMarais et al. | |
| 6,361,545 B1 | 3/2002 | Macoviak et al. | |
| 6,364,895 B1 | 4/2002 | Greenhalgh | |
| 6,375,668 B1 | 4/2002 | Gifford et al. | |
| 6,375,670 B1 | 4/2002 | Greenhalgh | |
| 6,383,205 B1 | 5/2002 | Samson et al. | |
| 6,383,206 B1 | 5/2002 | Gillick et al. | |
| 6,391,037 B1 | 5/2002 | Greenhalgh | |
| 6,402,771 B1 | 6/2002 | Palmer et al. | |
| 6,416,541 B2 | 7/2002 | Denardo | |
| 6,425,909 B1 | 7/2002 | Dieck et al. | |
| 6,428,558 B1 | 8/2002 | Jones et al. | |
| 6,432,122 B1 | 8/2002 | Gilson et al. | |
| 6,436,112 B2 | 8/2002 | Wensel et al. | |
| 6,458,139 B1 | 10/2002 | Palmer et al. | |
| 6,485,497 B2 | 11/2002 | Wensel et al. | |
| 6,485,501 B1 | 11/2002 | Green | |
| 6,485,502 B2 | 11/2002 | Don Michael et al. | |
| 6,488,701 B1 | 12/2002 | Nolting et al. | |
| 6,511,492 B1 | 1/2003 | Rosenbluth et al. | |
| 6,530,935 B2 | 3/2003 | Wensel et al. | |
| 6,530,939 B1 | 3/2003 | Hopkins et al. | |
| 6,540,768 B1 | 4/2003 | Diaz et al. | |
| 6,544,279 B1 | 4/2003 | Hopkins et al. | |
| 6,551,341 B2 | 4/2003 | Boylan et al. | |
| 6,551,342 B1 | 4/2003 | Shen et al. | |
| 6,575,996 B1 | 6/2003 | Denison et al. | |
| 6,575,997 B1 | 6/2003 | Palmer et al. | |
| 6,582,448 B1 | 6/2003 | Boyle et al. | |
| 6,585,756 B1 | 7/2003 | Strecker | |
| 6,589,265 B1 | 7/2003 | Palmer et al. | |
| 6,592,607 B1 | 7/2003 | Palmer et al. | |
| 6,592,614 B2 | 7/2003 | Lenker et al. | |
| 6,592,616 B1 | 7/2003 | Stack et al. | |

(56) References Cited

U.S. PATENT DOCUMENTS

| | | |
|---|---|---|
| 6,602,265 B2 | 8/2003 | Dubrul et al. |
| 6,602,271 B2 | 8/2003 | Adams et al. |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,632,241 B1 | 10/2003 | Hancock et al. |
| 6,638,245 B2 | 10/2003 | Miller et al. |
| 6,638,293 B1 | 10/2003 | Makower et al. |
| 6,641,590 B1 | 11/2003 | Palmer et al. |
| 6,656,218 B1 | 12/2003 | Denardo et al. |
| 6,660,021 B1 | 12/2003 | Palmer et al. |
| 6,663,650 B2 | 12/2003 | Sepetka et al. |
| 6,673,089 B1 | 1/2004 | Yassour et al. |
| 6,685,722 B1 | 2/2004 | Rosenbluth et al. |
| 6,692,504 B2 | 2/2004 | Kurz et al. |
| 6,692,508 B2 | 2/2004 | Wensel et al. |
| 6,692,509 B2 | 2/2004 | Wensel et al. |
| 6,695,858 B1 | 2/2004 | Dubrul et al. |
| 6,702,782 B2 | 3/2004 | Miller et al. |
| 6,702,834 B1 | 3/2004 | Boylan et al. |
| 6,709,465 B2 | 3/2004 | Mitchell et al. |
| 6,712,834 B2 | 3/2004 | Yassour et al. |
| 6,726,701 B2 | 4/2004 | Gilson et al. |
| 6,726,703 B2 | 4/2004 | Broome et al. |
| 6,730,104 B1 | 5/2004 | Sepetka et al. |
| 6,783,528 B2 | 8/2004 | Vincent-Prestigiacomo |
| 6,783,538 B2 | 8/2004 | McGuckin, Jr. et al. |
| 6,824,545 B2 | 11/2004 | Sepetka et al. |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer et al. |
| 6,913,618 B2 | 7/2005 | Denardo et al. |
| 6,939,361 B1 | 9/2005 | Kleshinski |
| 6,953,472 B2 | 10/2005 | Palmer et al. |
| 6,989,019 B2 | 1/2006 | Mazzocchi et al. |
| 6,989,021 B2 | 1/2006 | Bosma et al. |
| 6,994,718 B2 | 2/2006 | Groothuis et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,008,434 B2 | 3/2006 | Kurz et al. |
| 7,033,376 B2 | 4/2006 | Tsukernik |
| 7,041,116 B2 | 5/2006 | Goto et al. |
| 7,048,758 B2 | 5/2006 | Boyle et al. |
| 7,052,500 B2 | 5/2006 | Bashiri et al. |
| 7,058,456 B2 | 6/2006 | Pierce |
| 7,063,707 B2 | 6/2006 | Bose et al. |
| 7,083,633 B2 | 8/2006 | Morrill et al. |
| 7,083,822 B2 | 8/2006 | Brightbill |
| 7,094,249 B1 | 8/2006 | Broome et al. |
| 7,097,653 B2 | 8/2006 | Freudenthal et al. |
| 7,101,380 B2 | 9/2006 | Khachin et al. |
| 7,172,614 B2 | 2/2007 | Boyle et al. |
| 7,175,655 B1 | 2/2007 | Molaei |
| 7,179,273 B1 | 2/2007 | Palmer et al. |
| 7,185,922 B2 | 3/2007 | Takayanagi et al. |
| 7,220,271 B2 | 5/2007 | Clubb et al. |
| 7,226,464 B2 | 6/2007 | Garner et al. |
| 7,229,472 B2 | 6/2007 | DePalma et al. |
| 7,241,304 B2 | 7/2007 | Boyle et al. |
| 7,241,308 B2 | 7/2007 | Andreas et al. |
| 7,288,112 B2 | 10/2007 | Denardo et al. |
| 7,300,458 B2 | 11/2007 | Henkes et al. |
| 7,306,618 B2 | 12/2007 | Demond et al. |
| 7,314,483 B2 | 1/2008 | Andau et al. |
| 7,316,692 B2 | 1/2008 | Huffmaster |
| 7,323,001 B2 | 1/2008 | Clubb et al. |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins et al. |
| 7,425,215 B2 | 9/2008 | Boyle et al. |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka et al. |
| 7,556,636 B2 | 7/2009 | Mazzocchi et al. |
| 7,582,111 B2 | 9/2009 | Krolik et al. |
| 7,594,926 B2 | 9/2009 | Linder et al. |
| 7,604,649 B2 | 10/2009 | McGuckin, Jr. et al. |
| 7,604,650 B2 | 10/2009 | Bergheim |
| 7,618,434 B2 | 11/2009 | Santra et al. |
| 7,662,165 B2 | 2/2010 | Gilson et al. |
| 7,670,356 B2 | 3/2010 | Mazzocchi et al. |
| 7,678,123 B2 | 3/2010 | Chanduszko |
| 7,691,121 B2 | 4/2010 | Rosenbluth et al. |
| 7,691,124 B2 | 4/2010 | Balgobin |
| 7,708,770 B2 | 5/2010 | Linder et al. |
| 7,717,929 B2 | 5/2010 | Fallman |
| 7,736,385 B2 | 6/2010 | Agnew |
| 7,749,246 B2 | 7/2010 | McGuckin, Jr. et al. |
| 7,758,606 B2 | 7/2010 | Streeter et al. |
| 7,758,611 B2 | 7/2010 | Kato |
| 7,766,934 B2 | 8/2010 | Pal et al. |
| 7,771,452 B2 | 8/2010 | Pal et al. |
| 7,780,694 B2 | 8/2010 | Palmer et al. |
| 7,780,700 B2 | 8/2010 | Frazier et al. |
| 7,811,305 B2 | 10/2010 | Balgobin et al. |
| 7,815,659 B2 | 10/2010 | Conlon et al. |
| 7,819,893 B2 | 10/2010 | Brady et al. |
| 7,828,815 B2 | 11/2010 | Mazzocchi et al. |
| 7,828,816 B2 | 11/2010 | Mazzocchi et al. |
| 7,833,240 B2 | 11/2010 | Okushi et al. |
| 7,842,053 B2 | 11/2010 | Chanduszko et al. |
| 7,846,175 B2 | 12/2010 | Bonnette et al. |
| 7,846,176 B2 | 12/2010 | Gilson et al. |
| 7,850,708 B2 | 12/2010 | Pal |
| 7,883,516 B2 | 2/2011 | Huang et al. |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi et al. |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | OBrien et al. |
| 8,052,640 B2 | 11/2011 | Fiorella et al. |
| 8,057,497 B1 | 11/2011 | Raju et al. |
| 8,057,507 B2 | 11/2011 | Horan et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,118,856 B2 | 2/2012 | Schreck et al. |
| 8,123,769 B2 | 2/2012 | Osborne |
| 8,137,376 B2 | 3/2012 | Clubb et al. |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,262,689 B2 | 9/2012 | Schneiderman et al. |
| 8,282,668 B2 | 10/2012 | McGuckin, Jr. et al. |
| 8,298,257 B2 | 10/2012 | Sepetka et al. |
| RE43,882 E | 12/2012 | Hopkins et al. |
| 8,357,178 B2 | 1/2013 | Grandfield et al. |
| 8,357,179 B2 | 1/2013 | Grandfield et al. |
| 8,357,180 B2 | 1/2013 | Feller, III et al. |
| 8,357,893 B2 | 1/2013 | Xu et al. |
| 8,361,095 B2 | 1/2013 | Osborne |
| 8,361,110 B2 | 1/2013 | Chanduszko |

(56) References Cited

U.S. PATENT DOCUMENTS

| | | |
|---|---|---|
| 8,366,663 B2 | 2/2013 | Fiorella et al. |
| 8,409,215 B2 | 4/2013 | Sepetka et al. |
| 8,414,482 B2 | 4/2013 | Belson |
| 8,414,543 B2 | 4/2013 | McGuckin, Jr. et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,512,352 B2 | 8/2013 | Martin |
| 8,529,596 B2 | 9/2013 | Grandfield et al. |
| 8,545,526 B2 | 10/2013 | Martin et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,690,907 B1 | 4/2014 | Janardhan et al. |
| 8,696,622 B2 | 4/2014 | Fiorella et al. |
| 8,702,652 B2 | 4/2014 | Fiorella et al. |
| 8,702,704 B2 | 4/2014 | Shelton, IV et al. |
| 8,702,724 B2 | 4/2014 | Olsen et al. |
| 8,777,976 B2 | 7/2014 | Brady et al. |
| 8,777,979 B2 | 7/2014 | Shrivastava et al. |
| 8,784,434 B2 | 7/2014 | Rosenbluth et al. |
| 8,784,441 B2 | 7/2014 | Rosenbluth et al. |
| 8,795,305 B2 | 8/2014 | Martin et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,852,205 B2 | 10/2014 | Brady et al. |
| 8,870,941 B2 | 10/2014 | Evans et al. |
| 8,900,265 B1 | 12/2014 | Ulm, III |
| 8,920,358 B2 | 12/2014 | Levine et al. |
| 8,939,991 B2 | 1/2015 | Krolik et al. |
| 8,945,143 B2 | 2/2015 | Ferrera et al. |
| 8,945,160 B2 | 2/2015 | Krolik et al. |
| 8,945,169 B2 | 2/2015 | Pal |
| 8,945,172 B2 | 2/2015 | Ferrera et al. |
| 8,956,399 B2 | 2/2015 | Cam et al. |
| 8,968,330 B2 | 3/2015 | Rosenbluth et al. |
| 9,011,481 B2 | 4/2015 | Aggerholm et al. |
| 9,039,749 B2 | 5/2015 | Shrivastava et al. |
| 9,072,537 B2 | 7/2015 | Grandfield et al. |
| 9,095,342 B2 | 8/2015 | Becking et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,758 B2 | 10/2015 | Figulla et al. |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,211,132 B2 | 12/2015 | Bowman |
| 9,232,992 B2 | 1/2016 | Heidner et al. |
| 9,254,371 B2 | 2/2016 | Martin et al. |
| 9,301,769 B2 | 4/2016 | Brady et al. |
| 9,332,999 B2 | 5/2016 | Ray et al. |
| 9,402,707 B2 | 8/2016 | Brady et al. |
| 9,445,829 B2 | 9/2016 | Brady et al. |
| 9,456,834 B2 | 10/2016 | Folk |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,639 B2 | 5/2017 | Brady et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 * | 9/2017 | Bowman ............ A61B 17/221 |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,651 B2 | 10/2017 | Harrah et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,304 B2 | 12/2017 | Horan et al. |
| 9,833,604 B2 | 12/2017 | Lam et al. |
| 9,833,625 B2 | 12/2017 | Waldhauser et al. |
| 9,901,434 B2 | 2/2018 | Hoffman |
| 9,918,720 B2 | 3/2018 | Marchand et al. |
| 10,016,206 B1 | 7/2018 | Yang |
| 10,070,878 B2 | 9/2018 | Ma |
| 10,098,651 B2 | 10/2018 | Marchand et al. |
| 10,201,360 B2 | 2/2019 | Vale et al. |
| 10,231,751 B2 | 3/2019 | Sos |
| 10,292,723 B2 | 5/2019 | Brady et al. |
| 10,299,811 B2 | 5/2019 | Brady et al. |
| 10,363,054 B2 | 7/2019 | Vale et al. |
| 10,376,274 B2 | 8/2019 | Farin et al. |
| 10,390,850 B2 | 8/2019 | Vale et al. |
| 10,524,811 B2 | 1/2020 | Marchand et al. |
| 10,531,942 B2 | 1/2020 | Eggers |
| 10,617,435 B2 | 4/2020 | Vale et al. |
| 10,722,257 B2 | 7/2020 | Skillrud et al. |
| 10,856,684 B2 * | 12/2020 | Mauri ................ A47G 25/4053 |
| 11,439,418 B2 * | 9/2022 | O'Malley ............ A61B 17/221 |
| 11,517,340 B2 | 12/2022 | Casey |
| 2001/0003315 A1 | 5/2001 | Bates et al. |
| 2001/0016755 A1 | 8/2001 | Addis |
| 2001/0037141 A1 | 11/2001 | Yee et al. |
| 2001/0041909 A1 | 11/2001 | Tsugita et al. |
| 2001/0044632 A1 | 11/2001 | Daniel et al. |
| 2001/0049554 A1 | 12/2001 | Ruiz et al. |
| 2001/0051810 A1 | 12/2001 | Dubrul et al. |
| 2002/0004667 A1 | 1/2002 | Adams et al. |
| 2002/0016609 A1 | 2/2002 | Wensel et al. |
| 2002/0022859 A1 | 2/2002 | Hogendijk |
| 2002/0026211 A1 | 2/2002 | Khosravi et al. |
| 2002/0042627 A1 | 4/2002 | Brady et al. |
| 2002/0049468 A1 | 4/2002 | Streeter et al. |
| 2002/0052620 A1 | 5/2002 | Barbut |
| 2002/0058911 A1 | 5/2002 | Gilson et al. |

(56) References Cited

U.S. PATENT DOCUMENTS

| | | |
|---|---|---|
| 2002/0068954 A1 | 6/2002 | Foster |
| 2002/0072764 A1 | 6/2002 | Sepetka et al. |
| 2002/0082558 A1 | 6/2002 | Samson et al. |
| 2002/0091407 A1 | 7/2002 | Zando-Azizi et al. |
| 2002/0095171 A1 | 7/2002 | Belef |
| 2002/0123765 A1 | 9/2002 | Sepetka et al. |
| 2002/0128680 A1 | 9/2002 | Pavlovic |
| 2002/0138094 A1 | 9/2002 | Borillo et al. |
| 2002/0143349 A1 | 10/2002 | Gifford, III et al. |
| 2002/0143362 A1 | 10/2002 | Macoviak et al. |
| 2002/0156455 A1 | 10/2002 | Barbut |
| 2002/0161393 A1 | 10/2002 | Demond et al. |
| 2002/0165576 A1 | 11/2002 | Boyle et al. |
| 2002/0173819 A1 | 11/2002 | Leeflang et al. |
| 2002/0183787 A1 | 12/2002 | Wahr et al. |
| 2002/0188276 A1 | 12/2002 | Evans et al. |
| 2002/0188314 A1 | 12/2002 | Anderson et al. |
| 2002/0193824 A1 | 12/2002 | Boylan et al. |
| 2002/0198588 A1 | 12/2002 | Armstrong et al. |
| 2003/0004536 A1 | 1/2003 | Boylan et al. |
| 2003/0004538 A1 | 1/2003 | Secrest et al. |
| 2003/0004540 A1 | 1/2003 | Linder et al. |
| 2003/0004542 A1 | 1/2003 | Wensel et al. |
| 2003/0009146 A1 | 1/2003 | Muni et al. |
| 2003/0009191 A1 | 1/2003 | Wensel et al. |
| 2003/0038447 A1 | 2/2003 | Cantele |
| 2003/0040772 A1 | 2/2003 | Hyodoh et al. |
| 2003/0050663 A1 | 3/2003 | Khachin et al. |
| 2003/0069520 A1 | 4/2003 | Skujins et al. |
| 2003/0114879 A1 | 6/2003 | Euteneuer et al. |
| 2003/0125798 A1 | 7/2003 | Martin |
| 2003/0130682 A1 | 7/2003 | Broome et al. |
| 2003/0144687 A1 | 7/2003 | Brady et al. |
| 2003/0144688 A1 | 7/2003 | Brady et al. |
| 2003/0153943 A1 | 8/2003 | Michael et al. |
| 2003/0153944 A1 | 8/2003 | Phung et al. |
| 2003/0163064 A1 | 8/2003 | Vrba et al. |
| 2003/0163158 A1 | 8/2003 | White |
| 2003/0171769 A1 | 9/2003 | Barbut |
| 2003/0171771 A1 | 9/2003 | Anderson et al. |
| 2003/0176884 A1 | 9/2003 | Berrada et al. |
| 2003/0187495 A1 | 10/2003 | Cully et al. |
| 2003/0195537 A1 | 10/2003 | Dubrul et al. |
| 2003/0195554 A1 | 10/2003 | Shen et al. |
| 2003/0199917 A1 | 10/2003 | Knudson et al. |
| 2003/0204202 A1 | 10/2003 | Palmer et al. |
| 2003/0208224 A1 | 11/2003 | Broome |
| 2003/0212430 A1 | 11/2003 | Bose et al. |
| 2003/0236533 A1 | 12/2003 | Wilson et al. |
| 2004/0064179 A1 | 4/2004 | Linder et al. |
| 2004/0068288 A1 | 4/2004 | Palmer et al. |
| 2004/0073243 A1 | 4/2004 | Sepetka et al. |
| 2004/0079429 A1 | 4/2004 | Miller et al. |
| 2004/0082962 A1 | 4/2004 | Demarais et al. |
| 2004/0082967 A1 | 4/2004 | Broome et al. |
| 2004/0088001 A1 | 5/2004 | Bosma et al. |
| 2004/0093065 A1 | 5/2004 | Yachia et al. |
| 2004/0098050 A1 | 5/2004 | Foerster et al. |
| 2004/0133231 A1 | 7/2004 | Maitland et al. |
| 2004/0133232 A1 | 7/2004 | Rosenbluth et al. |
| 2004/0138692 A1 | 7/2004 | Phung et al. |
| 2004/0153117 A1 | 8/2004 | Clubb et al. |
| 2004/0153118 A1 | 8/2004 | Clubb et al. |
| 2004/0199201 A1 | 10/2004 | Kellett et al. |
| 2004/0204749 A1 | 10/2004 | Gunderson |
| 2004/0215318 A1 | 10/2004 | Kwitkin |
| 2004/0220663 A1 | 11/2004 | Rivelli |
| 2005/0010245 A1 | 1/2005 | Wasicek |
| 2005/0033348 A1 | 2/2005 | Sepetka et al. |
| 2005/0038447 A1 | 2/2005 | Huffmaster |
| 2005/0038468 A1 | 2/2005 | Panetta et al. |
| 2005/0043759 A1 | 2/2005 | Chanduszko |
| 2005/0049619 A1 | 3/2005 | Sepetka et al. |
| 2005/0049669 A1 | 3/2005 | Jones et al. |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059995 A1 | 3/2005 | Sepetka et al. |
| 2005/0085849 A1 | 4/2005 | Sepetka et al. |
| 2005/0090779 A1 | 4/2005 | Osypka |
| 2005/0090857 A1 | 4/2005 | Kusleika et al. |
| 2005/0125024 A1 | 6/2005 | Sepetka et al. |
| 2005/0171566 A1 | 8/2005 | Kanamaru |
| 2005/0192627 A1 | 9/2005 | Whisenant et al. |
| 2005/0215942 A1 | 9/2005 | Abrahamson et al. |
| 2005/0216030 A1 | 9/2005 | Sepetka et al. |
| 2005/0216050 A1 | 9/2005 | Sepetka et al. |
| 2005/0228417 A1 | 10/2005 | Teitelbaum et al. |
| 2005/0251154 A1* | 11/2005 | Chanduszko ...... A61B 17/0057 606/151 |
| 2005/0251206 A1 | 11/2005 | Maahs et al. |
| 2005/0251209 A1 | 11/2005 | Saadat et al. |
| 2005/0267491 A1 | 12/2005 | Kellett et al. |
| 2005/0273135 A1 | 12/2005 | Chanduszko et al. |
| 2005/0283186 A1 | 12/2005 | Berrada et al. |
| 2005/0288686 A1 | 12/2005 | Sepetka et al. |
| 2006/0009798 A1 | 1/2006 | Callister et al. |
| 2006/0009799 A1 | 1/2006 | Kleshinski et al. |
| 2006/0020285 A1 | 1/2006 | Niermann |
| 2006/0020286 A1 | 1/2006 | Niermann |
| 2006/0030877 A1 | 2/2006 | Martinez et al. |
| 2006/0041228 A1 | 2/2006 | Vo et al. |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0064151 A1 | 3/2006 | Guterman et al. |
| 2006/0069424 A1 | 3/2006 | Acosta et al. |
| 2006/0074477 A1 | 4/2006 | Berthiaume et al. |
| 2006/0142838 A1 | 6/2006 | Molaei et al. |
| 2006/0149313 A1 | 7/2006 | Arguello |
| 2006/0155305 A1 | 7/2006 | Freudenthal et al. |
| 2006/0161187 A1 | 7/2006 | Levine et al. |
| 2006/0195137 A1 | 8/2006 | Sepetka et al. |
| 2006/0224177 A1 | 10/2006 | Finitsis |
| 2006/0224179 A1 | 10/2006 | Kucharczyk et al. |
| 2006/0229638 A1 | 10/2006 | Abrams et al. |
| 2006/0235501 A1 | 10/2006 | Igaki |
| 2006/0241677 A1 | 10/2006 | Johnson et al. |
| 2006/0282111 A1 | 12/2006 | Morsi |
| 2006/0287668 A1 | 12/2006 | Fawzi et al. |
| 2006/0287701 A1 | 12/2006 | Pal |
| 2006/0293706 A1 | 12/2006 | Shimon |
| 2007/0010857 A1 | 1/2007 | Sugimoto et al. |
| 2007/0032879 A1 | 2/2007 | Levine et al. |
| 2007/0088382 A1 | 4/2007 | Bei et al. |
| 2007/0088383 A1 | 4/2007 | Pal et al. |
| 2007/0100348 A1 | 5/2007 | Cauthen, III et al. |
| 2007/0118173 A1 | 5/2007 | Magnuson et al. |
| 2007/0149997 A1 | 6/2007 | Muller |
| 2007/0156170 A1 | 7/2007 | Hancock et al. |
| 2007/0165170 A1 | 7/2007 | Fukuda |
| 2007/0179527 A1 | 8/2007 | Eskuri et al. |
| 2007/0191866 A1 | 8/2007 | Palmer et al. |
| 2007/0198028 A1 | 8/2007 | Miloslavski et al. |
| 2007/0198051 A1 | 8/2007 | Clubb et al. |
| 2007/0198075 A1 | 8/2007 | Levy |
| 2007/0208367 A1 | 9/2007 | Fiorella et al. |
| 2007/0208371 A1 | 9/2007 | French et al. |
| 2007/0225749 A1 | 9/2007 | Martin et al. |
| 2007/0233175 A1 | 10/2007 | Zaver et al. |
| 2007/0244505 A1 | 10/2007 | Gilson et al. |
| 2007/0270902 A1 | 11/2007 | Slazas et al. |
| 2007/0288054 A1 | 12/2007 | Tanaka et al. |
| 2008/0045881 A1 | 2/2008 | Teitelbaum et al. |
| 2008/0077227 A1 | 3/2008 | Ouellette et al. |
| 2008/0082107 A1 | 4/2008 | Miller et al. |
| 2008/0086190 A1 | 4/2008 | Ta |
| 2008/0091223 A1 | 4/2008 | Pokorney et al. |
| 2008/0097386 A1 | 4/2008 | Osypka |
| 2008/0109031 A1 | 5/2008 | Sepetka et al. |
| 2008/0109032 A1 | 5/2008 | Sepetka et al. |
| 2008/0119886 A1 | 5/2008 | Greenhalgh et al. |
| 2008/0125798 A1 | 5/2008 | Osborne et al. |
| 2008/0177296 A1 | 7/2008 | Sepetka et al. |

(56) References Cited

U.S. PATENT DOCUMENTS

| | | |
|---|---|---|
| 2008/0178890 A1 | 7/2008 | Townsend et al. |
| 2008/0183197 A1 | 7/2008 | Sepetka et al. |
| 2008/0183198 A1 | 7/2008 | Sepetka et al. |
| 2008/0183205 A1 | 7/2008 | Sepetka et al. |
| 2008/0188876 A1 | 8/2008 | Sepetka et al. |
| 2008/0188885 A1 | 8/2008 | Sepetka et al. |
| 2008/0188887 A1 | 8/2008 | Batiste |
| 2008/0200946 A1 | 8/2008 | Braun et al. |
| 2008/0200947 A1 | 8/2008 | Kusleika et al. |
| 2008/0215077 A1 | 9/2008 | Sepetka et al. |
| 2008/0221600 A1 | 9/2008 | Dieck et al. |
| 2008/0228209 A1 | 9/2008 | DeMello et al. |
| 2008/0234706 A1 | 9/2008 | Sepetka et al. |
| 2008/0243170 A1 | 10/2008 | Jenson et al. |
| 2008/0255596 A1 | 10/2008 | Jenson et al. |
| 2008/0262410 A1 | 10/2008 | Jenson et al. |
| 2008/0262528 A1 | 10/2008 | Martin |
| 2008/0262532 A1 | 10/2008 | Martin |
| 2008/0262590 A1 | 10/2008 | Murray |
| 2008/0269871 A1 | 10/2008 | Eli |
| 2008/0275488 A1 | 11/2008 | Fleming |
| 2008/0275493 A1 | 11/2008 | Farmiga |
| 2008/0281350 A1 | 11/2008 | Sepetka et al. |
| 2008/0312681 A1 | 12/2008 | Ansel et al. |
| 2009/0005858 A1 | 1/2009 | Young et al. |
| 2009/0024157 A1 | 1/2009 | Anukhin |
| 2009/0030443 A1 | 1/2009 | Buser et al. |
| 2009/0062841 A1 | 3/2009 | Amplatz et al. |
| 2009/0069828 A1 | 3/2009 | Martin et al. |
| 2009/0076539 A1 | 3/2009 | Valaie |
| 2009/0088793 A1 | 4/2009 | Bagaoisan et al. |
| 2009/0088795 A1 | 4/2009 | Cahill |
| 2009/0105722 A1 | 4/2009 | Fulkerson et al. |
| 2009/0105737 A1 | 4/2009 | Fulkerson et al. |
| 2009/0105747 A1 | 4/2009 | Chanduszko et al. |
| 2009/0149881 A1 | 6/2009 | Vale et al. |
| 2009/0163851 A1 | 6/2009 | Holloway et al. |
| 2009/0177206 A1 | 7/2009 | Lozier et al. |
| 2009/0182336 A1 | 7/2009 | Brenzel et al. |
| 2009/0281610 A1 | 11/2009 | Parker |
| 2009/0281619 A1 | 11/2009 | Le et al. |
| 2009/0287229 A1* | 11/2009 | Ogdahl ............ A61F 2/0063 606/232 |
| 2009/0292297 A1 | 11/2009 | Ferrere |
| 2009/0292307 A1 | 11/2009 | Razack |
| 2009/0299393 A1 | 12/2009 | Martin et al. |
| 2009/0299403 A1 | 12/2009 | Chanduszko et al. |
| 2009/0306702 A1 | 12/2009 | Miloslavski et al. |
| 2009/0326636 A1 | 12/2009 | Hashimoto et al. |
| 2010/0004607 A1 | 1/2010 | Wilson et al. |
| 2010/0076482 A1 | 3/2010 | Shu et al. |
| 2010/0087850 A1 | 4/2010 | Razack |
| 2010/0087908 A1 | 4/2010 | Hilaire et al. |
| 2010/0114017 A1 | 5/2010 | Lenker et al. |
| 2010/0125326 A1 | 5/2010 | Kalstad et al. |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnette et al. |
| 2010/0268265 A1 | 10/2010 | Krolik et al. |
| 2010/0274277 A1 | 10/2010 | Eaton |
| 2010/0318178 A1 | 12/2010 | Rapaport et al. |
| 2010/0324649 A1 | 12/2010 | Mattsson et al. |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009950 A1 | 1/2011 | Grandfield et al. |
| 2011/0015718 A1 | 1/2011 | Schreck |
| 2011/0022149 A1 | 1/2011 | Cox et al. |
| 2011/0040319 A1 | 2/2011 | Fulton, III |
| 2011/0054287 A1 | 3/2011 | Schultz |
| 2011/0054504 A1 | 3/2011 | Porter |
| 2011/0054514 A1 | 3/2011 | Arcand et al. |
| 2011/0054516 A1 | 3/2011 | Keegan et al. |
| 2011/0060212 A1 | 3/2011 | Slee et al. |
| 2011/0060359 A1 | 3/2011 | Hannes et al. |
| 2011/0106137 A1 | 5/2011 | Shimon |
| 2011/0125181 A1 | 5/2011 | Brady et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0184456 A1 | 7/2011 | Grandfield et al. |
| 2011/0196414 A1 | 8/2011 | Porter et al. |
| 2011/0202088 A1 | 8/2011 | Eckhouse et al. |
| 2011/0208233 A1 | 8/2011 | McGuckin, Jr. et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0224707 A1 | 9/2011 | Miloslavski et al. |
| 2011/0270374 A1 | 11/2011 | Orr et al. |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | di Palma et al. |
| 2012/0065660 A1 | 3/2012 | Ferrera et al. |
| 2012/0083823 A1 | 4/2012 | Shrivastava et al. |
| 2012/0083868 A1 | 4/2012 | Shrivastava et al. |
| 2012/0089216 A1 | 4/2012 | Rapaport et al. |
| 2012/0101510 A1 | 4/2012 | Lenker et al. |
| 2012/0116440 A1 | 5/2012 | Leynov et al. |
| 2012/0123466 A1 | 5/2012 | Porter et al. |
| 2012/0022572 A1 | 6/2012 | Braun et al. |
| 2012/0143230 A1 | 6/2012 | Sepetka et al. |
| 2012/0143237 A1 | 6/2012 | Cam et al. |
| 2012/0143317 A1 | 6/2012 | Cam et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0209312 A1 | 8/2012 | Aggerholm et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2012/0330350 A1 | 12/2012 | Jones et al. |
| 2013/0030460 A1 | 1/2013 | Marks et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144311 A1 | 6/2013 | Fung et al. |
| 2013/0144326 A1 | 6/2013 | Brady et al. |
| 2013/0158591 A1 | 6/2013 | Koehler |
| 2013/0158592 A1 | 6/2013 | Porter |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0325051 A1 | 12/2013 | Martin et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0046359 A1 | 2/2014 | Bowman et al. |
| 2014/0088678 A1 | 3/2014 | Wainwright et al. |
| 2014/0121672 A1 | 5/2014 | Folk |
| 2014/0128905 A1 | 5/2014 | Molaei |
| 2014/0134654 A1 | 5/2014 | Rudel et al. |
| 2014/0135812 A1 | 5/2014 | Divino et al. |
| 2014/0142598 A1 | 5/2014 | Fulton, III |
| 2014/0163367 A1 | 6/2014 | Eskuri |
| 2014/0180122 A1 | 6/2014 | Stigall et al. |
| 2014/0180377 A1 | 6/2014 | Bose et al. |
| 2014/0180397 A1 | 6/2014 | Gerberding et al. |
| 2014/0194911 A1 | 7/2014 | Johnson et al. |
| 2014/0194919 A1 | 7/2014 | Losordo et al. |
| 2014/0200607 A1 | 7/2014 | Sepetka et al. |
| 2014/0200608 A1 | 7/2014 | Brady et al. |
| 2014/0236220 A1 | 8/2014 | Inoue |

(56) References Cited

U.S. PATENT DOCUMENTS

| | | |
|---|---|---|
| 2014/0243881 A1 | 8/2014 | Lees et al. |
| 2014/0257362 A1 | 9/2014 | Eidenschink |
| 2014/0276922 A1 | 9/2014 | McLain et al. |
| 2014/0277013 A1* | 9/2014 | Sepetka ............. A61B 17/3207 606/159 |
| 2014/0277079 A1 | 9/2014 | Vale et al. |
| 2014/0303667 A1 | 10/2014 | Cox et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0032144 A1 | 1/2015 | Holloway |
| 2015/0080937 A1 | 3/2015 | Davidson |
| 2015/0112376 A1 | 4/2015 | Molaei et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0224133 A1 | 8/2015 | Ohri et al. |
| 2015/0250497 A1 | 9/2015 | Marks et al. |
| 2015/0257775 A1 | 9/2015 | Gilvarry et al. |
| 2015/0272716 A1 | 10/2015 | Pinchuk et al. |
| 2015/0297252 A1 | 10/2015 | Miloslavski et al. |
| 2015/0313617 A1 | 11/2015 | Grandfield et al. |
| 2015/0320431 A1 | 11/2015 | Ulm |
| 2015/0352325 A1 | 12/2015 | Quick |
| 2015/0359547 A1 | 12/2015 | Vale et al. |
| 2015/0366650 A1 | 12/2015 | Zi et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0045298 A1 | 2/2016 | Thinnes, Jr. et al. |
| 2016/0066921 A1 | 3/2016 | Seifert et al. |
| 2016/0100928 A1 | 4/2016 | Lees et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0303381 A1 | 10/2016 | Pierce et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020542 A1 | 1/2017 | Martin et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0056061 A1 | 3/2017 | Ogle et al. |
| 2017/0071614 A1* | 3/2017 | Vale ........................ A61F 2/013 |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0112647 A1 | 4/2017 | Sachar et al. |
| 2017/0113023 A1 | 4/2017 | Steingisser et al. |
| 2017/0119409 A1 | 5/2017 | Ma |
| 2017/0143465 A1 | 5/2017 | Ulm, III |
| 2017/0147765 A1 | 5/2017 | Mehta |
| 2017/0150979 A1 | 6/2017 | Ulm |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0189041 A1 | 7/2017 | Cox et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0140315 A1 | 5/2018 | Bowman et al. |
| 2018/0206865 A1 | 7/2018 | Martin et al. |
| 2018/0207399 A1 | 7/2018 | Chou et al. |
| 2018/0263650 A1* | 9/2018 | Iwanami ................. B21F 15/06 |
| 2018/0325537 A1 | 11/2018 | Shamay et al. |
| 2018/0326024 A1 | 11/2018 | Prochazka et al. |
| 2018/0344338 A1* | 12/2018 | Brady ..................... A61F 2/013 |
| 2019/0000492 A1* | 1/2019 | Casey ................. A61B 17/221 |
| 2019/0015061 A1 | 1/2019 | Liebeskind et al. |
| 2019/0167284 A1 | 6/2019 | Friedman et al. |
| 2019/0239907 A1 | 8/2019 | Brady et al. |
| 2019/0292273 A1 | 9/2019 | Hanotin et al. |

(56) References Cited

U.S. PATENT DOCUMENTS

| | | |
|---|---|---|
| 2019/0374239 A1 | 12/2019 | Martin et al. |
| 2019/0380723 A1 | 12/2019 | Grandfield et al. |
| 2019/0388097 A1 | 12/2019 | Girdhar et al. |
| 2020/0000483 A1 | 1/2020 | Brady et al. |
| 2020/0009150 A1 | 1/2020 | Chamorro Sanchez |
| 2020/0085444 A1 | 3/2020 | Vale et al. |
| 2020/0100804 A1 | 4/2020 | Casey et al. |
| 2020/0297364 A1 | 9/2020 | Choe et al. |
| 2020/0390459 A1 | 12/2020 | Casey et al. |
| 2021/0005321 A1 | 1/2021 | Hwang |
| 2021/0007757 A1 | 1/2021 | Casey et al. |
| 2021/0228223 A1 | 7/2021 | Casey et al. |
| 2022/0192739 A1 | 6/2022 | Deen et al. |

FOREIGN PATENT DOCUMENTS

| | | |
|---|---|---|
| CN | 102307613 A | 1/2012 |
| CN | 102316809 A | 1/2012 |
| CN | 102596098 A | 7/2012 |
| CN | 103764049 A | 4/2014 |
| CN | 104042304 A | 9/2014 |
| CN | 105208950 A | 12/2015 |
| CN | 105662532 A | 6/2016 |
| CN | 205359559 U | 7/2016 |
| CN | 107530090 A | 1/2018 |
| CN | 208582467 U | 3/2019 |
| DE | 202009001951 U1 | 3/2010 |
| DE | 102009056450 A1 | 6/2011 |
| DE | 102010010849 A1 | 9/2011 |
| DE | 102010014778 A1 | 10/2011 |
| DE | 102010024085 A1 | 12/2011 |
| DE | 102011014586 B3 | 9/2012 |
| EP | 1153581 A1 | 11/2001 |
| EP | 2301450 A1 | 3/2011 |
| EP | 2438891 A1 | 4/2012 |
| EP | 2628455 A1 | 8/2013 |
| EP | 3156004 A1 | 4/2017 |
| EP | 3593742 A1 | 1/2020 |
| EP | 3669802 A1 | 6/2020 |
| EP | 3858291 A1 | 8/2021 |
| ES | 2210456 T3 | 7/2004 |
| GB | 2427554 A | 1/2007 |
| GB | 2494820 A | 3/2013 |
| JP | 09-19438 A | 1/1997 |
| JP | 2014-511223 A | 5/2014 |
| JP | 2014-525796 A | 10/2014 |
| JP | 2015-505250 A | 2/2015 |
| JP | 2016-513505 A | 5/2016 |
| JP | 2019-526365 A | 9/2019 |
| WO | WO 94/24926 A1 | 11/1994 |
| WO | WO 97/27808 A1 | 8/1997 |
| WO | WO 97/38631 A1 | 10/1997 |
| WO | WO 99/20335 A1 | 4/1999 |
| WO | WO 99/56801 A2 | 11/1999 |
| WO | WO 99/60933 A1 | 12/1999 |
| WO | WO 01/21077 A1 | 3/2001 |
| WO | WO 02/02162 A2 | 1/2002 |
| WO | WO 02/11627 A2 | 2/2002 |
| WO | WO 02/43616 A2 | 6/2002 |
| WO | WO 02/070061 A1 | 9/2002 |
| WO | WO 02/094111 A2 | 11/2002 |
| WO | WO 03/002006 A1 | 1/2003 |
| WO | WO 03/030751 A1 | 4/2003 |
| WO | WO 03/051448 A2 | 6/2003 |
| WO | WO 2004/028571 A2 | 4/2004 |
| WO | WO 2004/056275 A1 | 7/2004 |
| WO | WO 2005/000130 A1 | 1/2005 |
| WO | WO 2005/027779 A2 | 3/2005 |
| WO | WO 2006/021407 A2 | 3/2006 |
| WO | WO 2006/031410 A2 | 3/2006 |
| WO | WO 2006/107641 A2 | 10/2006 |
| WO | WO 2006/135823 A2 | 12/2006 |
| WO | WO 2007/054307 A2 | 5/2007 |
| WO | WO 2007/068424 A2 | 6/2007 |
| WO | WO 2008/034615 A2 | 3/2008 |
| WO | WO 2008/051431 A1 | 5/2008 |
| WO | WO 2008/131116 A1 | 10/2008 |
| WO | WO 2008/135823 A1 | 11/2008 |
| WO | WO 2009/031338 A1 | 3/2009 |
| WO | WO 2009/076482 A1 | 6/2009 |
| WO | WO 2009/086482 A1 | 7/2009 |
| WO | WO 2009/105710 A1 | 8/2009 |
| WO | WO 2010/010545 A1 | 1/2010 |
| WO | WO 2010/046897 A1 | 4/2010 |
| WO | WO 2010/075565 A2 | 7/2010 |
| WO | WO 2010/102307 A1 | 9/2010 |
| WO | WO 2010/146581 A1 | 12/2010 |
| WO | WO 2011/013556 A1 | 2/2011 |
| WO | WO 2011/066961 A1 | 6/2011 |
| WO | WO 2011/082319 A1 | 7/2011 |
| WO | WO 2011/095352 A1 | 8/2011 |
| WO | WO 2011/106426 A1 | 9/2011 |
| WO | WO 2011/110316 A1 | 9/2011 |
| WO | WO 2011/135556 A1 | 11/2011 |
| WO | WO 2012/052982 A1 | 4/2012 |
| WO | WO 2012/064726 A1 | 5/2012 |
| WO | WO 2012/081020 A1 | 6/2012 |
| WO | WO 2012/110619 A1 | 8/2012 |
| WO | WO 2012/120490 A2 | 9/2012 |
| WO | WO 2012/156924 A1 | 11/2012 |
| WO | WO 2013/016435 A1 | 1/2013 |
| WO | WO 2013/072777 A2 | 5/2013 |
| WO | WO 2013/105099 A2 | 7/2013 |
| WO | WO 2013/109756 A2 | 7/2013 |
| WO | WO 2013/187927 A1 | 12/2013 |
| WO | WO 2014/047650 A1 | 3/2014 |
| WO | WO 2014/081892 A1 | 5/2014 |
| WO | WO 2014/139845 A1 | 9/2014 |
| WO | WO 2014/169266 A1 | 10/2014 |
| WO | WO 2014/178198 A1 | 11/2014 |
| WO | WO 2015/061365 A1 | 4/2015 |
| WO | WO 2015/103547 A1 | 7/2015 |
| WO | WO 2015/134625 A1 | 9/2015 |
| WO | WO 2015/179324 A2 | 11/2015 |
| WO | WO 2015/189354 A1 | 12/2015 |
| WO | WO 2016/010995 A1 | 1/2016 |
| WO | WO 2016/089451 A1 | 6/2016 |
| WO | WO 2017/089424 A1 | 6/2017 |
| WO | WO 2017/090473 A1 | 6/2017 |
| WO | WO 2017/103686 A2 | 6/2017 |
| WO | WO 2017/161204 A1 | 9/2017 |
| WO | WO 2020/039082 A1 | 2/2020 |
| WO | WO 2021/113302 A1 | 6/2021 |

OTHER PUBLICATIONS

Arai, D., et al. "Histological examination of vascular damage caused by stent retriever thrombectomy devices" J NeuroIntervent Surg 8:992-995 (2016).

Eugéne, F., et al. "One-Year MR Angiographic and Clinical Follow-Up after Intracranial Mechanical Thrombectomy Using a Stent Retriever Device" AJNR 126-132 (2015).

Loh, Y., et al. "Recanalization Rates Decrease with Increasing Thrombectomy Attempts" AJNR Am J Neuroradiol 31:935-939 (2010).

* cited by examiner

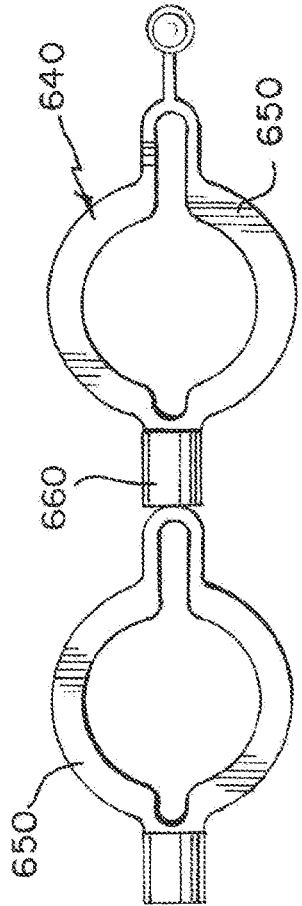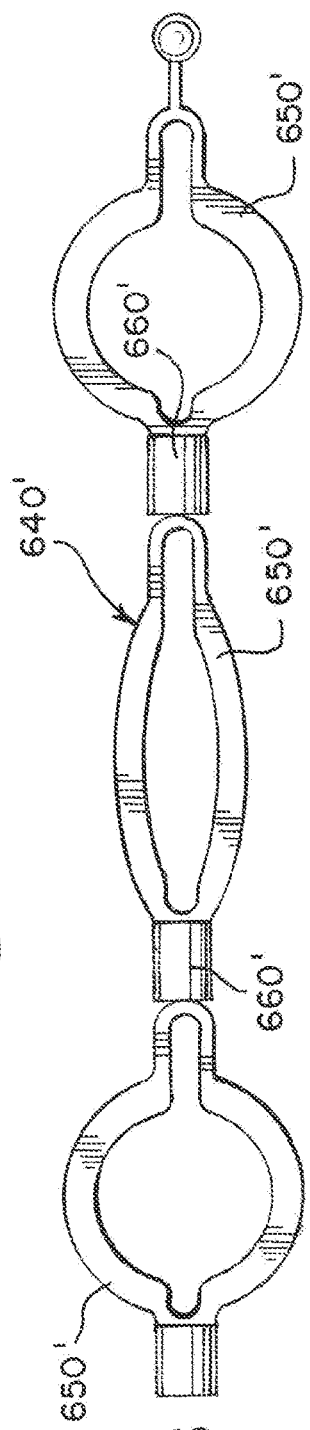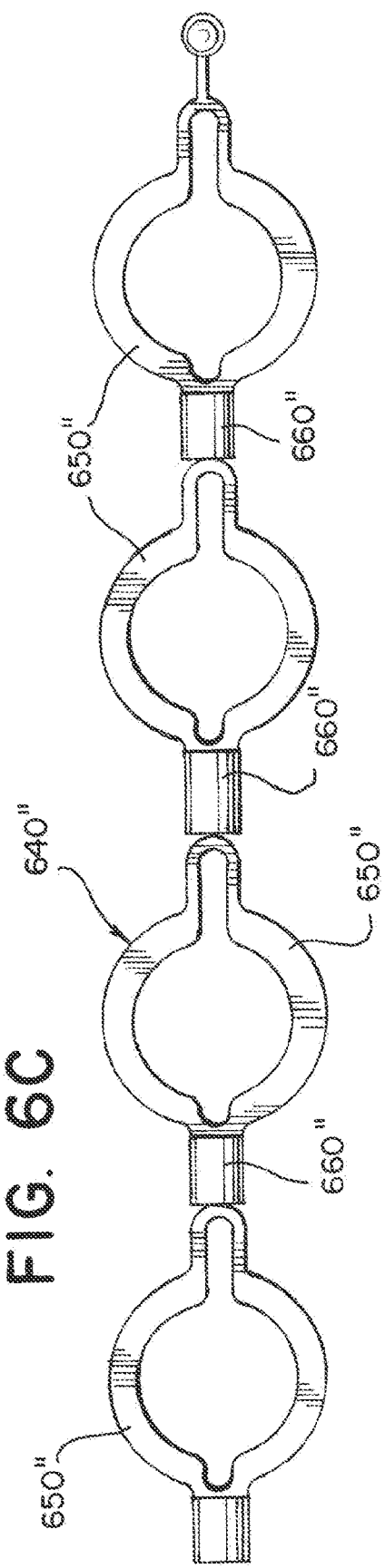

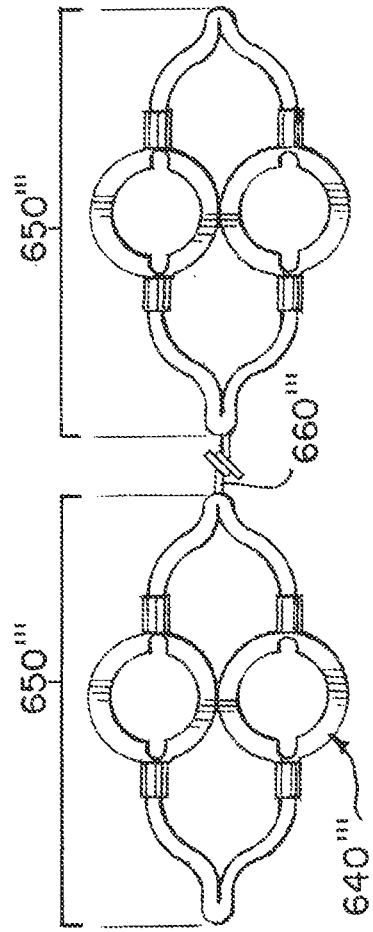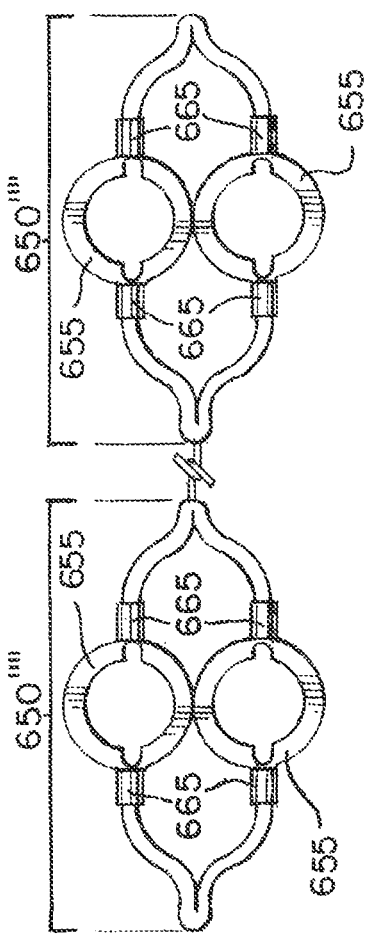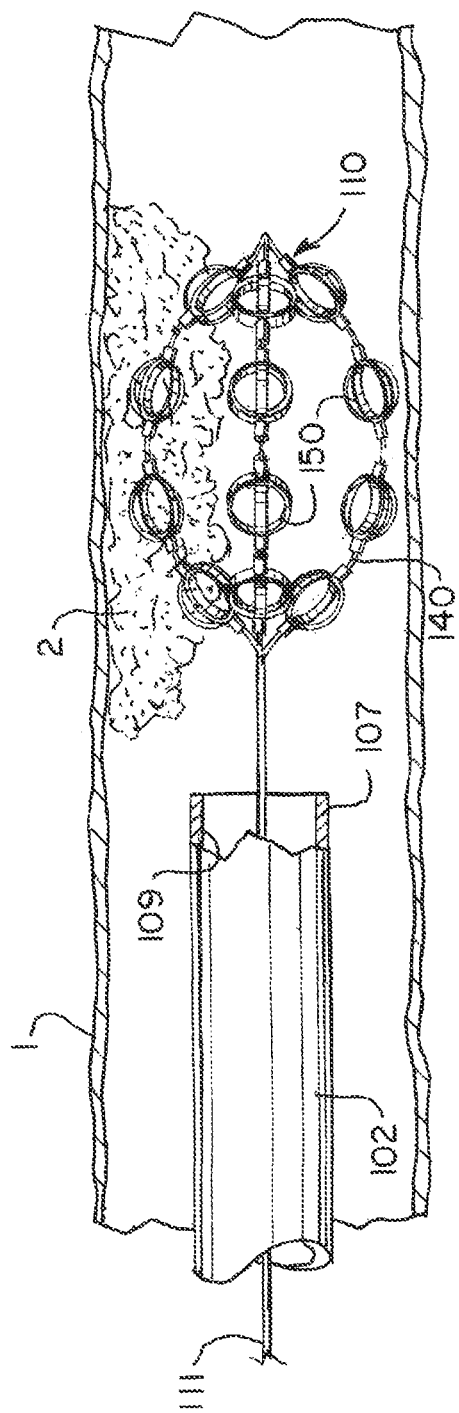

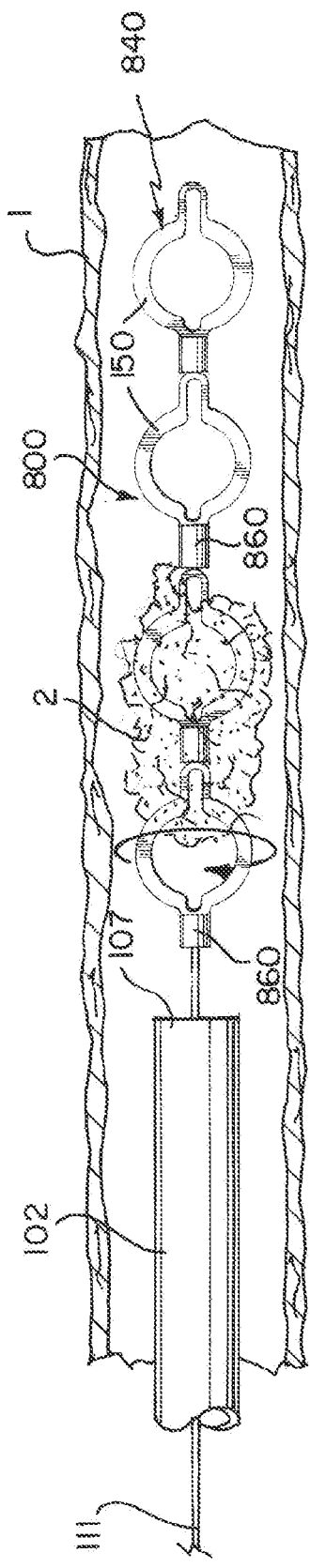
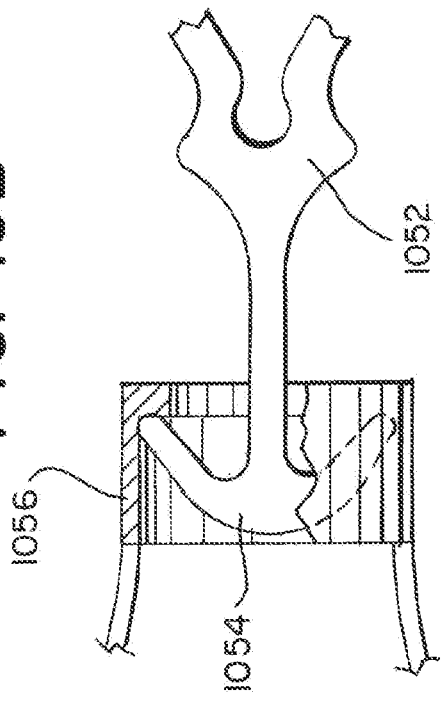
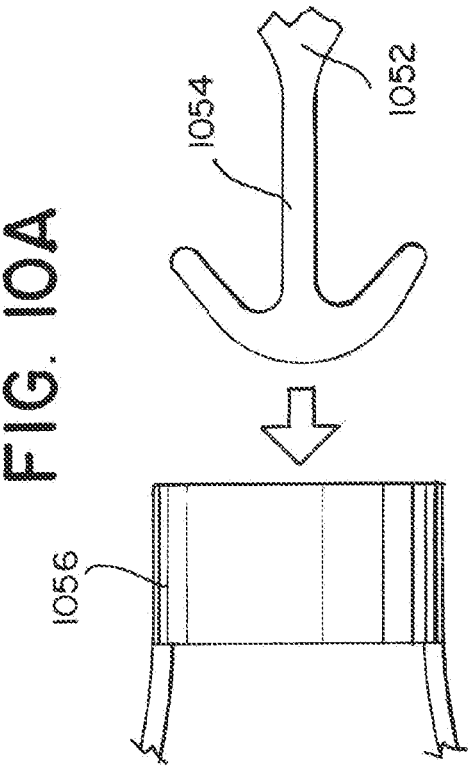

SELF-ORIENTING ROTATING STENTRIEVER PINCHING CELLS

FIELD

The present application relates generally to clot retrieval devices, and self-orienting pinching cells and stentrievers containing the same.

BACKGROUND

The World Health Organization estimates that 15,000,000 blood clots occur annually. Clots may develop and block vessels locally without being released in the form of an embolus—this mechanism is common in the formation of coronary blockages. Acute obstructions may include blood clots, misplaced devices, migrated devices, large emboli, and the like. Thromboembolism occurs when part or all of a thrombus breaks away from the blood vessel wall. This clot is then carried in the direction of blood flow. Clots can include a range of morphologies and consistencies. Long strands of softer clot material may tend to lodge at bifurcations or trifurcations, resulting in multiple vessels being simultaneously occluded over significant lengths.

Of the 15,000,000 clots that occur annually, one-third of patients die, and another one-third are disabled. Currently, a number of mechanical recanalization devices are in clinical use. First generation devices included the Merci Retriever device. Newer devices based on stent-like technology, referred to as "stentrievers" or "stent-retrievers", are currently displacing these first generation thrombectomy devices for recanalization in acute ischemic stroke.

There are significant challenges associated with designing clot removal devices that can deliver high levels of performance. There are also a number of access challenges that make it difficult to deliver devices. For example, the vasculature in the area in which the clot may be lodged is often fragile and delicate and neurovascular vessels are more fragile than similarly sized vessels in other parts of the body and are in a soft tissue bed. Excessive tensile forces applied on these vessels could result in perforations and hemorrhage. Pulmonary vessels are larger than those of the cerebral vasculature, but are also delicate in nature, particularly those more distal vessels.

Stent-like clot retriever devices are being increasingly used to remove clots from cerebral vessels of acute stroke patients, but such devices are not without disadvantages. A stent-like clot retriever often relies on its outward radial force to grip the clot. If the radial force is too low, the device will lose its grip on the clot. If the radial force is too high, the device may damage the vessel wall and may require too much force to withdraw. Such devices that have sufficient radial force to deal with all clot types may therefore cause vessel trauma and serious patient injury, and retrievers that have appropriate radial force to remain atraumatic may not be able to effectively handle all clot types. In this respect, retriever devices may differ in size, shape, and physical properties, such as radial force, as discussed above, ease of deployment, friction, radiopacity, and interaction with vessel wall. See, Loh Y, Jahan R, McArthur D. *Recanalization rates decrease with increasing thrombectomy attempts.* American Journal . . . 2010 May; 31(5):935-9; and Arai D, Ishii A, Chihara H, Ikeda H, Miyamoto S. *Histological examination of vascular damage caused by stent retriever thrombectomy devices*, J Neurointery Surg. 2016 October; 8(10):992-5. Some designs have also been based on in-vitro stroke models that incorporate realistic clot analogs derived from animal blood that represent the wide range of human clots retrieved from stroke patients. See, Eugène F, Gauvrit J-Y, Ferré J-C, Gentric J-C, Besseghir A, Ronzière T, et al. *One-year MR angiographic and clinical follow-up after intracranial mechanical thrombectomy using a stent retriever device*, AJNR Am J Neuroradiol. 2015 January; 36(1):126-32 (18), each of which is incorporated by reference herein in their entirety.

Though success rates are high when utilizing mechanical thrombectomy, there are still a proportion of patients for which adequate reperfusion cannot be achieved, certainly, in part, due to the clot not being retrieved. Cell orientation is a major influencing factor in forming a successful pinch with a microcatheter and stentriever. Certain solutions of this disclosure address these and other issues of the art.

SUMMARY

It is an object of the present designs to provide devices and methods to meet the above-stated needs. The designs can be for a clot retrieval device capable of removing a clot from utilizing rotational pinching cells.

In some examples, there is provided a clot removal device for removing a clot from a body vessel, the clot removal device including: an elongated member sized to traverse vasculature and having a proximal end and a distal end, the elongated member comprising a longitudinal axis; and an engagement structure connected to the distal end of the elongated member, the engagement structure comprising a plurality of pinching cells connected to each other.

In some examples, the plurality of pinching cells are configured to engage the clot in an expanded deployed configuration and to pinch the clot upon actuation to a clot pinching configuration.

In some examples, a first pinching cell of the plurality of pinching cells is connected to a second pinching cell of the plurality of pinching cells such that the second pinching cell is rotatable respective the first pinching cell substantially about the longitudinal axis.

In some examples, the engagement structure is non-tubular.

In some examples, at least one of the plurality of pinching cells includes a double pinching cell.

In some examples, the second pinching cell is fully rotatable respective to the first pinching cell.

In some examples, the second pinching cell is rotatable respective the first pinching cell across an angle of about 180 degrees.

In some examples, the second pinching cell is rotatable respective the first pinching cell across an angle of about 90 degrees.

In some examples, a connection of the first pinching cell to the second pinching cell biases a rotational offset between the first pinching cell the first and second pinching cells.

In some examples, the biased rotational offset between the first and second pinching cells is between about 30 to about 150 degrees.

In some examples, the first pinching cell comprises a collar, and the second pinching cell comprises a mating connector configured to rotatably connect with the collar.

In some examples, the mating connector comprises collapsible fingers for insertion into the collar.

In some examples, the plurality of pinching cells comprise alternating collar pinching cells and joiner pinching cells, the collar pinching cells comprising collars on a first end and a second end of the collar pinching cells, and the joiner pinching cells comprising mating connectors configured to rotatably connect with the collars on a first end and a second end of the joiner pinching cells.

In some examples, each of the plurality of pinching cells comprises a mating connector on a first end and a collar on a second end, the mating connector being configured to rotatably connect with the collar.

In some examples, a third pinching cell of the plurality of pinching cells is connected to the second pinching cell such that the third pinching cell is rotatable respective to the second pinching cell.

In some examples, a degree of rotation of the third pinching cell respective the second pinching cell is less than a degree of rotation of the second pinching cell respective the first pinching cell.

In some examples, a degree of rotation of the third pinching cell respective the second pinching cell is greater than a degree of rotation of the second pinching cell respective the first pinching cell.

In some examples, the first pinching cell is connected to the distal end of the elongated member such that the first pinching cell is rotatable respective to the elongated member.

In some examples, the plurality of pinching cells has three or fewer pinching cells in a chain of pinching cells.

In some examples, the plurality of pinching cells has two or fewer pinching cells in the chain of pinching cells.

In some examples, there is provided a clot removal device for removing a clot from a body vessel, the clot removal device including: an elongated member sized to traverse vasculature and having a proximal end and a distal end, the elongated member defining a longitudinal axis; and an engagement structure connected to the distal end of the elongated member, the engagement structure comprising a pinching cell configured to engage the clot in an expanded deployed configuration and to pinch the clot upon actuation to a clot pinching configuration.

In some examples, the pinching cell is connected to the elongated member such that the pinching cell is rotatable respective the elongated member substantially about the longitudinal axis.

In some examples, there is provided a method for manufacturing a clot removal device, the method including: forming a plurality of pinching cells, each of the plurality of pinching cells comprising connection means to rotatably connect to at least one other pinching cell of the plurality of pinching cells; connecting a first pinching cell of the plurality of pinching cells to an elongated member sized to traverse vasculature, the elongated member defining a longitudinal axis; and connecting a second pinching cell of the plurality of pinching cells to the first pinching cell via the respective connection means of the first pinching cell and the second pinching cell.

In some examples, there is provided a method for retrieving a clot, the method including: deploying a pinching portion of a clot retrieval device into an expanded state from a collapsed state within a blood vessel and proximate the clot, the clot retrieval device including an elongated member having a distal end, the elongated member defining a longitudinal axis; and the pinching portion located proximate the distal end and comprising a plurality of pinching cells including a first pinching cell disposed proximate the distal end, and a second pinching cell rotatably connected to the first pinching cell substantially about the longitudinal axis, the pinching portion being operable to pinch the clot when transitioning from an expanded deployed configuration to a pinching configuration.

In some examples, the method further includes: advancing a lumen of a microcatheter over the pinching portion such that at least one of the plurality of pinching cells at least partially collapses into the lumen of the microcatheter; and pinching the pinching portion in contact with the portion of the clot upon actuation to the pinching configuration until a portion of the clot is compressed between the pinching portion and the microcatheter.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

FIGS. 6A-6E illustrate example pinch cell chains according to example embodiments.

FIGS. 7A and 7B illustrate an operation of a microcatheter and stentriever according to aspects of the present disclosure.

FIGS. 9A and 9B illustrate an operation of a microcatheter and stentriever according to aspects of the present disclosure.

FIGS. 10A and 10B illustrate connecting of adjacent cells according to aspects of the present disclosure.

DETAILED DESCRIPTION

Figure 1:
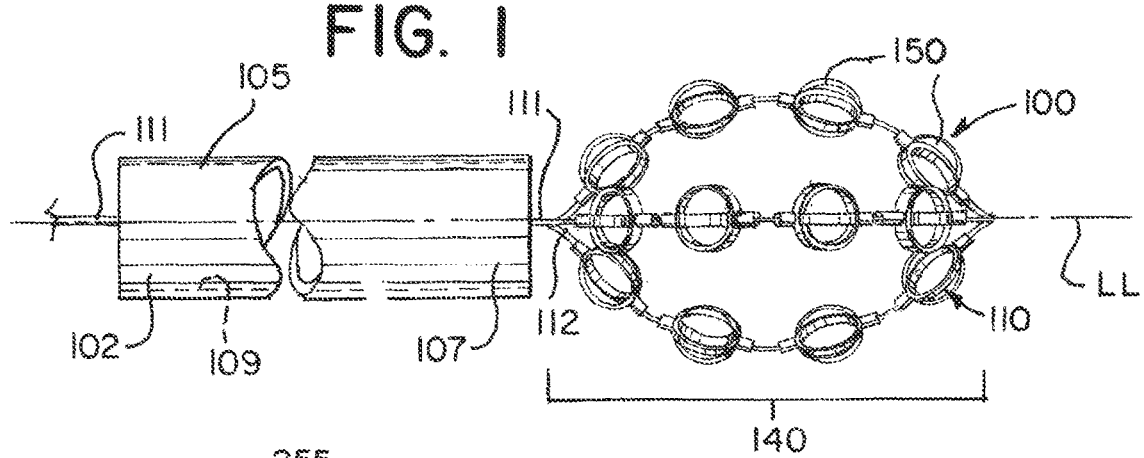
FIG. 1 illustrates a stentriever and microcatheter according to aspects of the present disclosure.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology were resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 71% to 99%.

As discussed herein, the vasculature of a "subject" or "patient" may be vasculature of a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient, for example.

As discussed herein, "operator" may include a doctor, surgeon, or any other individual or delivery instrumentation associated with delivery of a clot revascularization device to the vasculature of a subject.

As discussed herein, "thrombus" can be understood as a clot in the circulatory system that remains in a site of the vasculature hindering or otherwise obstructing flow in a blood vessel. The terms, "clot", "thrombus", "obstruction", "occlusion", "blockage", and/or the like, can be and are often used interchangeably throughout this disclosure.

Delivery of a "revascularization device" is typically accomplished via delivery of one or more catheters into the femoral artery and/or the radial artery, guided into the arteries of the brain, vascular bypass, angioplasty, and/or the like. "Revascularization devices" can include, but not be limited to, one or more stents, stentrievers, clot removal devices, clot revascularization devices, aspiration systems, one or more combinations thereof, and/or the like, each of which are often used interchangeably throughout this disclosure.

FIG. 1 illustrates a stentriever and microcatheter 100 (e.g., a clot removal device 100) according to aspects of the present disclosure. Clot removal device 100 may include microcatheter 102 and a stentriever 110. Microcatheter 102 has a proximal end 105 and a distal end 107 disposed opposite thereof. Microcatheter 120 includes a lumen 109 passing from the proximal end 105 to the distal end 107.

Stentriever 110 may include an engagement structure 140 and an elongated member 111 (e.g., a structural thread 111) defining a longitudinal axis L-L. The engagement structure 140 may include at least a first and a second pinching cell 150. For example, engagement structure 140 may include a chain of pinching cells 150 connected to a distal end 112 of the structural thread 144. In a delivery configuration, the engagement structure 140 may be disposed within lumen 109 within the microcatheter 102. Once delivered, the engagement structure 140 may be extended from the microcatheter 102 (e.g., via a hand control or a push-pull mechanism). At least one of the pinching cells 150 may be configured to be rotationally independent, e.g., of adjacent cells 150 and/or the structural thread 111. For example, as struts of the pinching cells 150 expand into clots, the pinching cell 150 deflects, causing rotation of the pinching cell 150-formed cage to improve integration of the clot into the pinching cell 150. This may lead to a greater likelihood of successful pinching of the clot by the pinching cell 150.

Figure 2A:
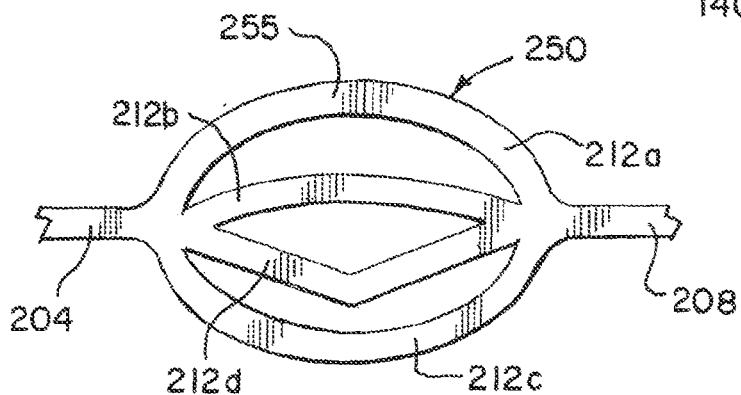
FIGS. 2A-2C illustrate example pinching cells according to aspects of the present disclosure.
Figure 2B:
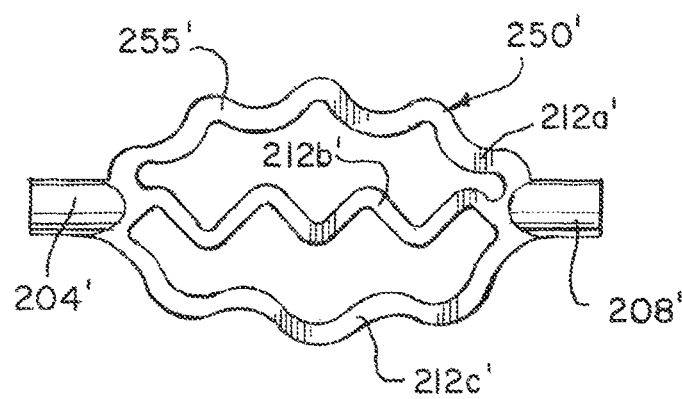
Figure 2C:
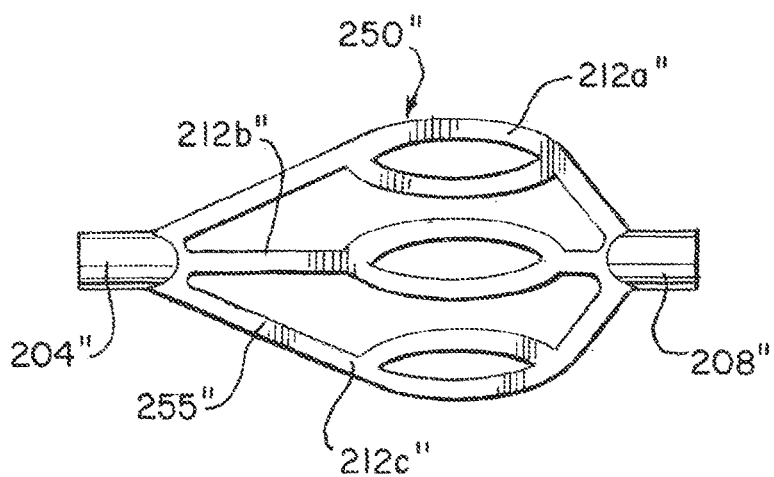

FIGS. 2A-2C illustrate example pinching cells 250 according to aspects of the present disclosure. Referring to FIG. 2A, pinching cell 250 may have a first end 204, a second end 208 disposed on the opposite side thereof, and a generally cylindrical capturing portion 255 disposed therein. The capturing portion 255 may include a plurality of arms 212a-212d (e.g., struts), creating a cage therebetween. The arms 212a-212d may have a substantially arced shape be configured to capture a clot within the cage. The first end 204 and the second end 208 may be configured to connect to one or more neighboring pinching cells and/or structural thread 111.

Referring to FIG. 2B, pinching cell 250' may have a first end 204', a second end 208' disposed on the opposite side thereof, and a generally flat capturing portion 255' disposed therein. The capturing portion 255' may include a plurality of arms 212a'-212c' (e.g., struts), creating a cage therebetween. The arms 212a'-212c' may have waved shape that may, in some cases, improve capture characteristics.

Referring to FIG. 2C, pinching cell 250" may have a first end 204', a second end 208' disposed on the opposite side thereof, and a generally capturing portion 255" disposed therein. The capturing portion 255" may include a plurality of cells 212a"-212c" (e.g., struts), creating a plurality of cage spaces therebetween. The cells 212a"-212c" may each have a substantially ovular shape and be connected to the first end 204' and the second end 208' via arms.

Figure 3A:
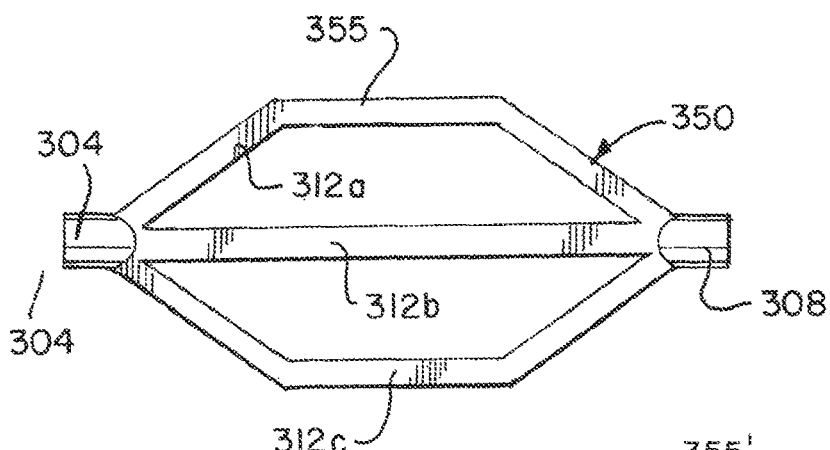
FIGS. 3A-3B illustrate example pinching cells according to aspects of the present disclosure.
Figure 3B:
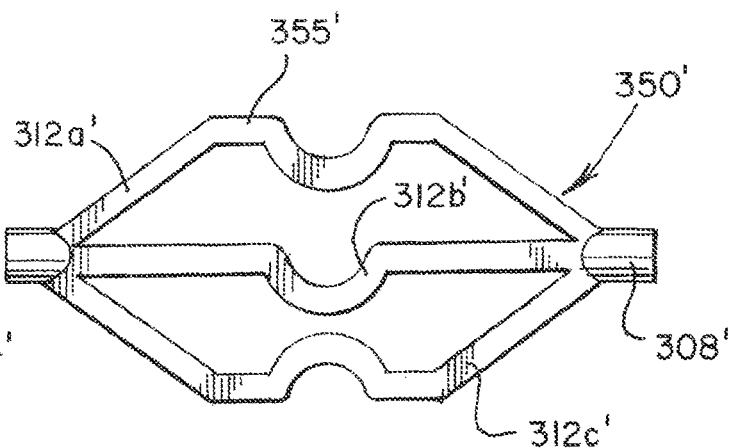

FIGS. 3A-3B illustrate example pinching cells 350 according to aspects of the present disclosure. Referring to FIG. 3A, pinching cell 250 may have a first end 304, a second end 308 disposed on the opposite side thereof, and a generally hexagonal capturing portion 355 disposed therein. The capturing portion 355 may include a plurality of arms 312a-312c (e.g., struts), creating a cage therebetween. The arms 312a-312c may have substantially straight edges configured to capture a clot within the cage.

Referring to FIG. 3B, pinching cell 350' may have a first end 304', a second end 308' disposed on the opposite side thereof, and a capturing portion 355' disposed therein. The capturing portion 355' may include a plurality of arms 312a'-312c' (e.g., struts), creating a cage therebetween. The arms 312a'-312c' may have generally straight edges with one or more indentions, for example, formed proximate a middle portion of the capturing portion 355'.

Although specific connector types have been described above with reference to FIGS. 2A-3B, one of ordinary skill will recognize that the pinch cells may be replaced with similar or alternative pinch cells without departing from the scope of the present disclosure.

Figure 4A:
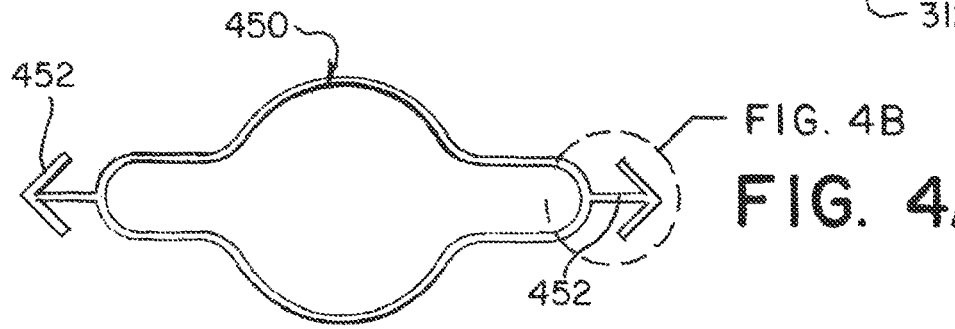
FIGS. 4A-5C illustrate example pinching cell connection configurations according to aspects of the present disclosure.
Figure 4B:
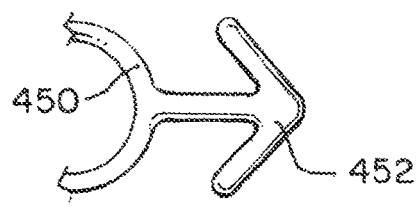
Figure 4C:
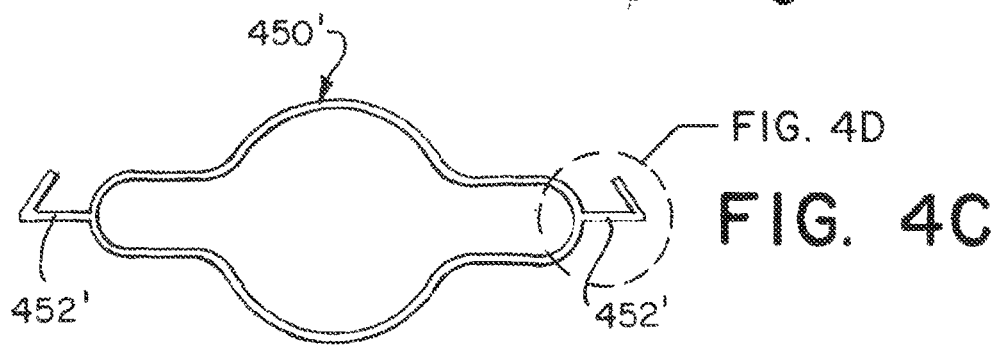
Figure 4D:
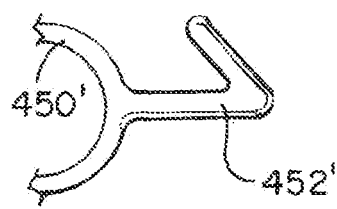
Figure 4E:
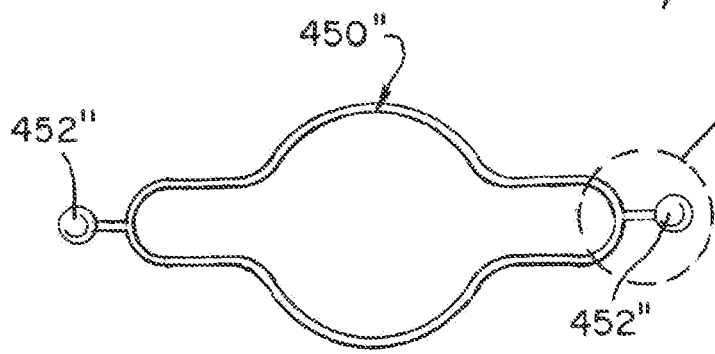
Figure 4F:
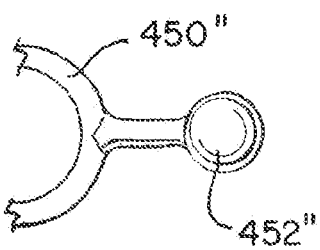

FIGS. 4A-5C illustrate example pinching cell connection configurations for pinching cells 450 and 550 according to aspects of the present disclosure. Referring to FIG. 4A, pinching cell 450 may include a t-style connector 452 on each end (e.g., a joiner pinching cell). The t-style connector 452 (FIG. 4B) may be configured to allow approximately 90-degree rotation relative to a connecting structure (e.g., a connecting pinching cell and/or thread 111). The t-style connector 452 may have two fingers extending from a central portion. Referring to FIG. 4C, pinching cell 450' may include a hook-style connector 452' on each end (e.g., a joiner pinching cell). The hook-style connector 452' (FIG. 4D) may be configured to allow approximately 180-degree rotation relative to a connecting structure (e.g., a connecting pinching cell and/or thread 111). The hook-style connector 452' may have a single finger extending from a central portion. Referring to FIG. 4E, pinching cell 450" may include a hook-style connector 452" on each end (e.g., a joiner pinching cell). The ball-joint connector 452" (FIG. 4F) may be configured to allow substantially free rotation (e.g., 360 degrees) relative to a connecting structure (e.g., a connecting pinching cell and/or thread 111). The ball-joint connector 452" may have a ball-joint formed on an end of a central portion.

Figure 5A:
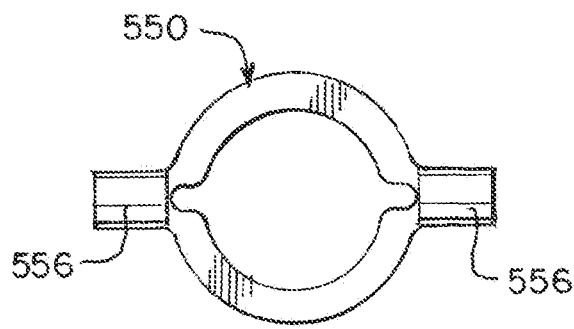
Figure 5B:
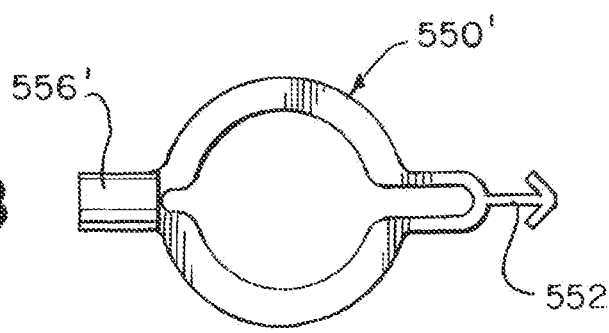
Figure 5C:
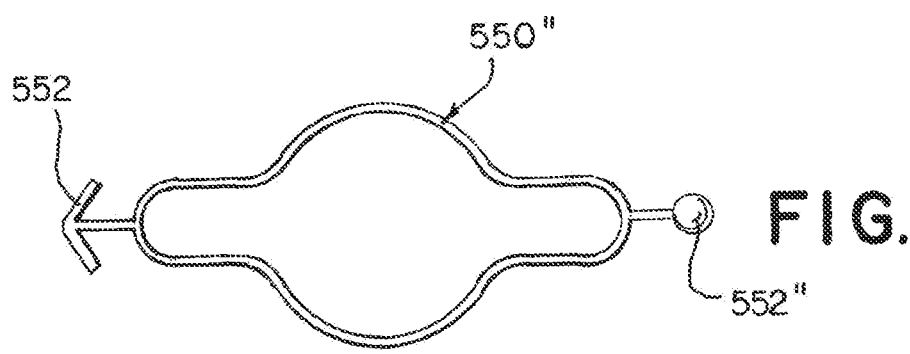

Referring to FIG. 5A, pinching cell 550 may include a collar connector 556 (e.g., a collar) on each end (e.g., a collar pinching cell 550). Collar connector 556 may be configured to connect to, for example, a t-style connector 452, a hook-style connector 452', and/or a ball-joint connector 452" of a connecting structure (e.g., a connecting pinching cell and/or thread 111). The collar connector 556 may be adaptable to allow different relative rotation based on a type of connected connector. Referring to FIG. 5B, pinching cell 550' may include a collar connector 556' on one end and a t-style connector 552 on the other end. The collar connector 556' may be configured to connect to a mating connector of a neighboring pinch cell and/or thread 111. The t-style connector 552, may be configured to connect to a collar connector of a neighboring pinch cell and/or thread 111. In this way, a single type of cell may be made and connected to for a chain of pinch cells. Referring to FIG. 5C, pinching cell 550" may include a t-style connector 552 on one end and a ball-style connector 552" on the other end (e.g., a joiner pinching cell). In this way, pinching cell 550" may be configured to have different relative rotational characteristics to neighboring cells and/or threads 111 on the opposite side of pinching cell 550".

In some cases, connections may bias certain rotational offsets between neighboring cells 150. For example, in some cases, a biased rotational offset between the first and second pinching cells may be between about 30 to about 150 degrees or between about 150 and 210 degrees. Although specific connector types have been described above with reference to FIGS. 4A-5C, one of ordinary skill will recognize that the types of connectors may be replaced with similar or alternative connectors without departing from the scope of the present disclosure.

FIGS. 6A-6E illustrate example pinch cell chains 640 according to example embodiments. Referring to FIG. 6A, pinching cell chain 640 may have two pinch cells 650 relatively rotatable about connection 660. Depending on the type of connection, cells 650 may be relatively rotatable by about 90 degrees, about 180 degrees, or about 360 degrees, but these are merely examples. Referring to FIG. 6B, pinching cell chain 640' may have three pinch cells 650' attached via connections 660'. Depending on the type of connection, cells 650' may be relatively rotatable to neighboring cells by about 90 degrees, about 180 degrees, or about 360 degrees, but these are merely examples. In some cases, different neighboring cells 650' may have different rotational characteristics. For example, first and second cells 650' may be relatively rotatable by 180 degrees, while second and third cells may be relatively rotatable by 90 degrees or be substantially rotationally fixed. IN FIG. 6B, neighboring cells may have a biased rotational offset, for example, between 150 and 210 degrees. Referring to FIG. 6C, pinching cell chain 640" may have four or more pinch cells 650" attached via connections 660". Depending on a type of connection, cells 650" may be relatively rotatable to neighboring cells by about 90 degrees, about 180 degrees, or about 360 degrees, but these are merely examples. In some cases, different neighboring cells 650" may have different rotational characteristics.

Referring to FIG. 6D, pinching cell chain 640''' may have two double-celled pinch cells 650''' attached via connections 660'''. Depending on a type of connection, cells 650''' may be relatively rotatable to neighboring cells by about 90 degrees, about 180 degrees, or about 360 degrees, but these are merely examples. Referring to FIG. 6E, pinching cell chain 640'''' may have two double pinching cells 650'''' attached via connections 660''''. Within the double-cell structure 650'''', the individual pinching cells 655 may also be relatively rotatable via connections 665 depending on a type of connection, cells 650''' may be relatively rotatable to neighboring cells by about 90 degrees, about 180 degrees, or about 360 degrees, but these are merely examples. The use of double pinching cells may be considered a non-tubular engagement structure.

Figure 7B:
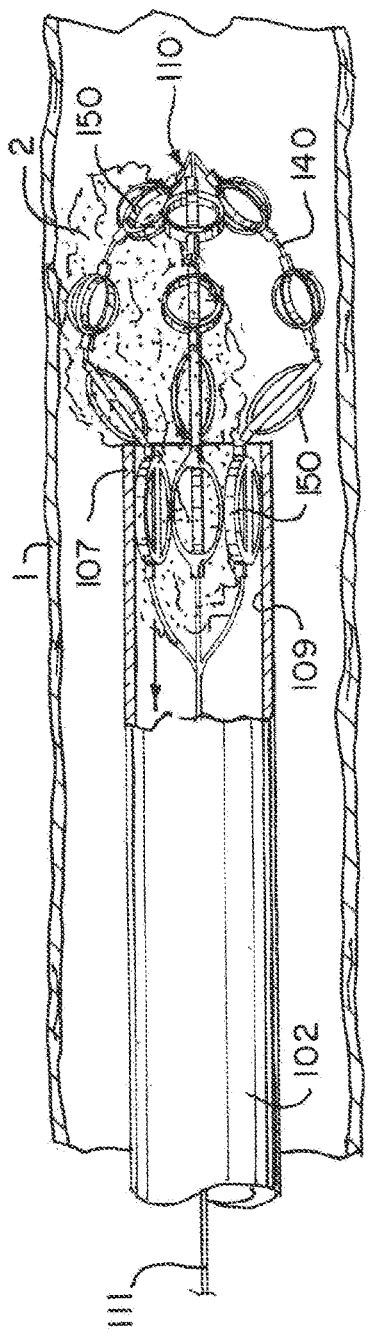

FIGS. 7A and 7B illustrate an operation of a microcatheter 102 and stentriever 110 according to aspects of the present disclosure. Microcatheter 102 and stentriever 110 may be moved within a blood vessel 1 to clot 2. The engagement structure 140 may be positioned within the microcatheter 102, e.g., in a collapsed configuration. Once positioned correctly, engagement structure 140 may be extended from microcatheter 102. The engagement structure 140 may interfere with clot 2. The engagement structure 140 may then be partially retracted into microcatheter 102, for example, as shown in FIG. 7B. Accordingly, engagement structure 140 may pinch clot 2 against microcatheter 102 (e.g., in a pinching configuration).

Figure 8:
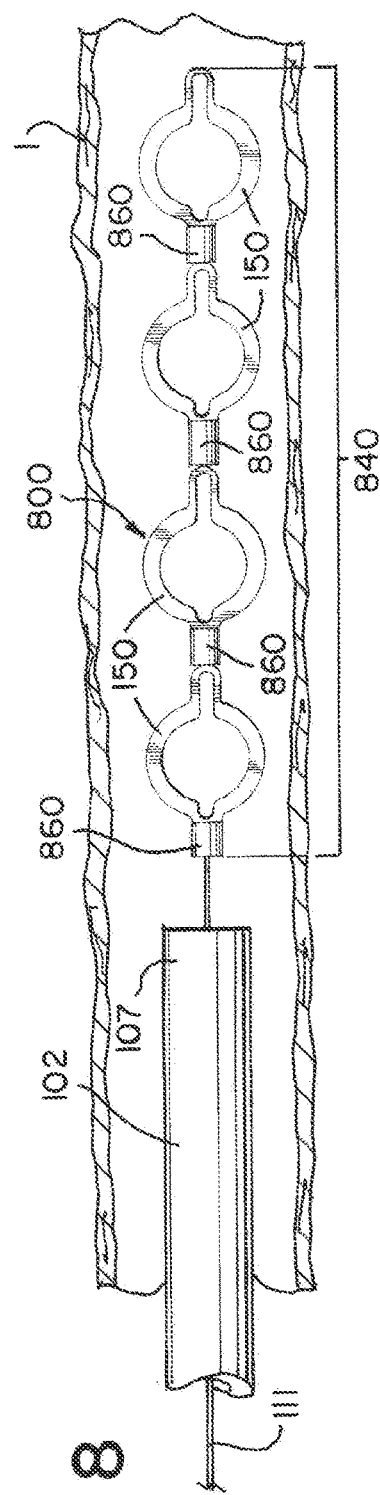
FIG. 8 illustrates a stentriever and microcatheter according to aspects of the present disclosure.

FIG. 8 illustrates a stentriever and microcatheter 800 (e.g., a clot removal device 800) according to aspects of the present disclosure. Clot removal device 800 may include microcatheter 102 and a stentriever 110. Stentriever 110 may include an engagement structure 840, including a single chain of pinch cells 150. The chain of pinching cells 150 connected to a distal end 112 of the structural thread 144. In a delivery configuration, the engagement structure 840 may be disposed within microcatheter 102. Once delivered, the engagement structure 840 may be extended from the microcatheter 102 (e.g., via a hand control or a push-pull mechanism). At least one of the pinching cells 150 may be configured to be rotationally independent, e.g., of adjacent cells 150 and/or the structural thread 111 via connections 860. For example, as struts of the pinching cells 150 expand into clots, the pinching cell 150 deflects, causing rotation of the pinching cell 150 cage to improve integration of the clot into the pinching cell 150. This may lead to a greater likelihood of successful pinching of the clot by the pinching cell 150 as compared to relatively fixed pinching cells.

Figure 9A:
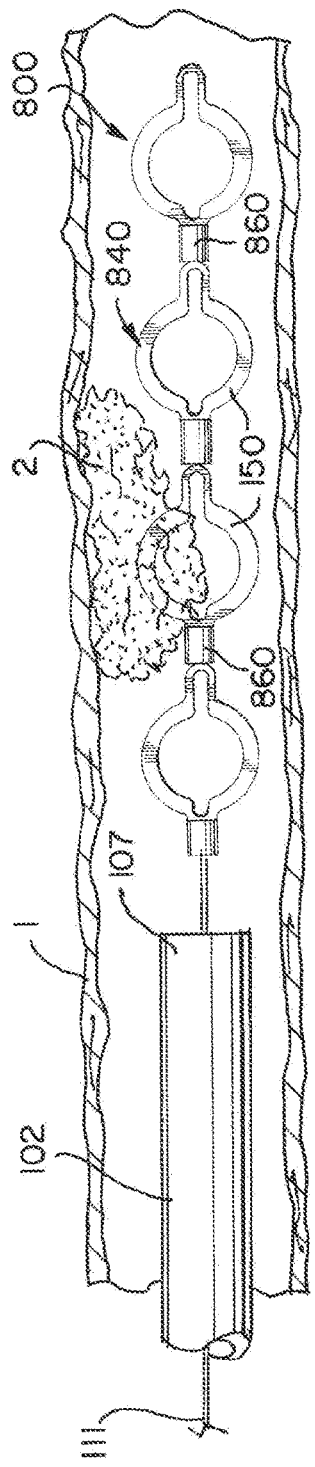

FIGS. 9A and 9B illustrate an operation of a microcatheter 102 and stentriever 110 according to aspects of the present disclosure. Microcatheter 102 and stentriever 110 may be moved within a blood vessel 1 to clot 2. The engagement structure 840 may be positioned within the microcatheter 102, e.g., in a collapsed configuration. Once positioned correctly, engagement structure 840 may be extended from microcatheter 102. The engagement structure 840 may interfere with clot 2, for example, by a cell 150 rotating and increasing inference therewith. The engagement structure 840 may then be partially retracted into microcatheter 102, for example, as shown in FIG. 7B. Accordingly, engagement structure 840 may pinch clot 2 against microcatheter 102 (e.g., in a pinching configuration).

FIGS. 10A and 10B illustrate connecting of adjacent cells according to aspects of the present disclosure. A cell with a collar connector 1056 and a cell with a t-style connector 1052 are provided (FIG. 10A). The t-style connector 1052 is inserted into the collar connector. The fingers 1054 of the t-style connector 1052 deform (e.g., be collapsible fingers) and expand once the first cell and the second cell are combined (FIG. 10B). Thereafter, the t-style connector may have certain rotational freedom such that the first and the second cell are rotationally independent (for example, over 90 degrees). Although t-style and collar connectors are discussed, one of ordinary skill would recognize that various different or alternative cell connectors and connection mechanisms may be employed without departing from the scope of the present disclosure.

Figure 11:
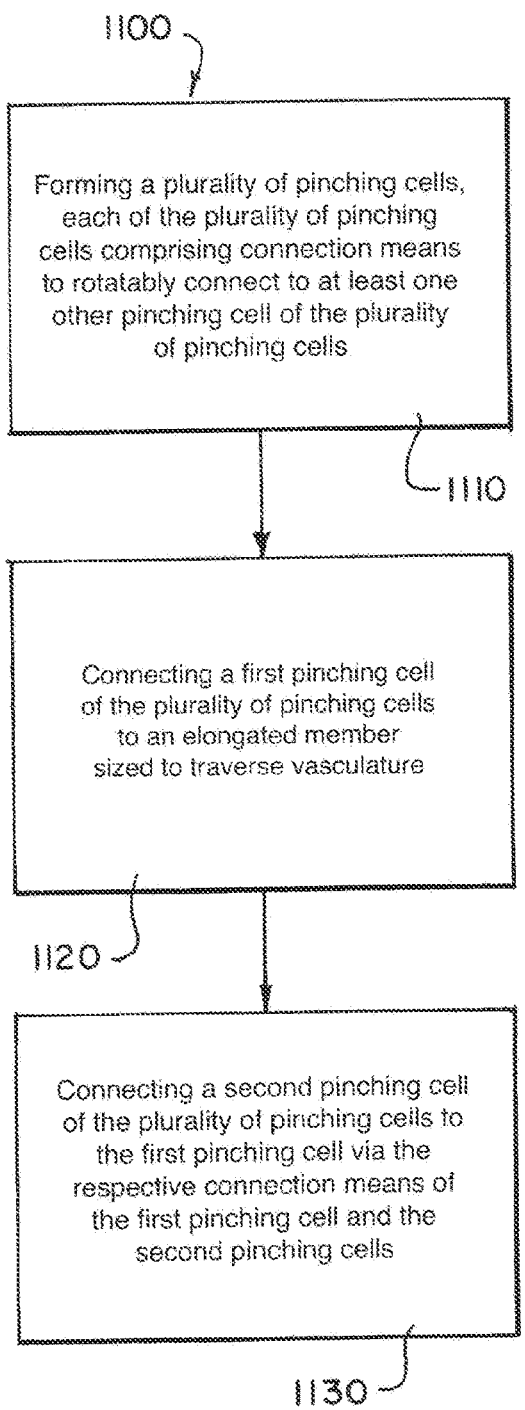
FIG. 11 is a flowchart of producing a stentriever according to aspects of the present disclosure.

FIG. 11 is a flowchart 1100 of producing a stentriever according to aspects of the present disclosure. The method may include forming 1110 a plurality of pinching cells (e.g., pinching cell 150). Each of the plurality of pinching cells comprising connection means to rotatably connect to at least one other pinching cell of the plurality of pinching cells. A first pinching cell of the plurality of pinching cells may be connected 1120 to an elongated member (e.g., thread 111) that is sized to traverse vasculature. Then, a second pinching cell (e.g., cell 150) of the plurality of pinching cells may be connected 1130 to the first pinching cell via the respective connection means of the first pinching cell and the second pinching cells. Additional cells 150 may be connected 130 until a chain of desired length is formed.

Figure 12:
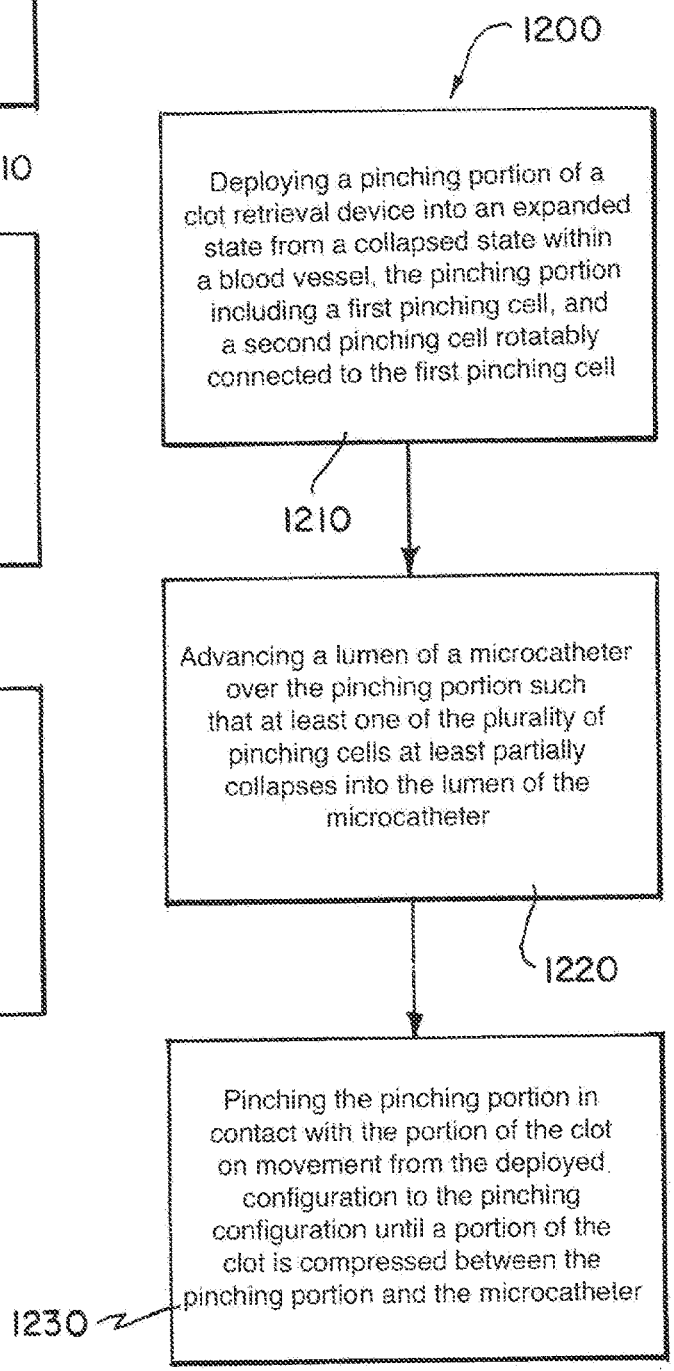
FIG. 12 is a flowchart of a treatment incorporating an example clot removal device according to aspects of the present disclosure.

FIG. 12 is a flowchart 1200 of a treatment incorporating an example clot removal device (e.g., combination stentriever and microcatheter 100 or 800) according to aspects of the present disclosure. The method includes deploying a pinching portion 140 of a clot retrieval device into an expanded state from a collapsed state within a blood vessel 1, the pinching portion including a first pinching cell, and a second pinching cell rotatably connected to the first pinching cell. The clot removal device may be a microcatheter and stentriever (e.g., 100 or 800) and may include a microcatheter (e.g., 102) and a stentriever (e.g., 110). A lumen 109 of the microcatheter may be advanced 1220 over the pinching portion 140 such that at least one of the plurality of pinching cells at least partially collapses into the lumen 109 of the microcatheter 102.

The pinching portion 140 may be pinched 1230 in contact with the portion of the clot 2 on movement from the deployed configuration to the pinching configuration until a portion of the clot 2 is compressed between the pinching portion 140 and the microcatheter 102. The clot removal device may then be withdrawn from the blood vessel with the clot 2.

The descriptions contained herein are examples of embodiments of the invention and are not intended in any way to limit the scope of the invention. As described herein, the invention contemplates many variations and modifications of the catheter 100 and methods for manufacturing and using the same. Additional modifications that are apparent to those having skill in the art to which this invention pertains and are intended to be within the scope of the claims which follow.

What is claimed is:

1. A clot removal device for removing a clot from a body vessel, the clot removal device comprising:

an elongated member sized to traverse vasculature and having a proximal end and a distal end, the elongated member comprising a longitudinal axis; and an engagement structure connected to the distal end of the elongated member, the engagement structure comprising a plurality of pinching cells connected to each other, the plurality of pinching cells being configured to engage the clot in an expanded deployed configuration and to pinch the clot upon actuation to a clot pinching configuration, a first pinching cell of the plurality of pinching cells being connected to a second pinching cell of the plurality of pinching cells such that the second pinching cell is rotatable respective to the first pinching cell substantially about the longitudinal axis, wherein the plurality of pinching cells comprise alternating collar pinching cells and joiner pinching cells, the collar pinching cells comprising collars on a first end and a second end of the collar pinching cells, and the joiner pinching cells comprising mating connectors configured to rotatably connect with the collars on a first end and a second end of the joiner pinching cells.

2. The clot removal device of claim 1, wherein the engagement structure is non-tubular.

3. The clot removal device of claim 1, wherein at least one of the plurality of pinching cells comprises a double pinching cell.

4. The clot removal device of claim 1, wherein the second pinching cell is fully rotatable respective to the first pinching cell.

5. The clot removal device of claim 1, wherein the second pinching cell is rotatable respective to the first pinching cell across an angle of about 180 degrees.

6. The clot removal device of claim 1, wherein the second pinching cell is rotatable respective to the first pinching cell across an angle of about 90 degrees.

7. The clot removal device of claim 1, wherein a connection of the first pinching cell to the second pinching cell biases a rotational offset between the first pinching cell the first and second pinching cells.

8. The clot removal device of claim 7, wherein the biased rotational offset between the first and second pinching cells is between about 30 to about 150 degrees.

9. The clot removal device of claim 1, wherein the first pinching cell comprises a collar and the second pinching cell comprises a mating connector configured to rotatably connect with the collar.

10. The clot removal device of claim 9, wherein the mating connector comprises collapsible fingers for insertion into the collar.

11. The clot removal device of claim 1, wherein each of the plurality of pinching cells comprise a mating connector on a first end and a collar on a second end, the mating connector being configured to rotatably connect with the collar.

12. The clot removal device of claim 1, wherein a third pinching cell of the plurality of pinching cells is connected to the second pinching cell such that the third pinching cell is rotatable respective to the second pinching cell.

13. The clot removal device of claim 12, wherein a degree of rotation of the third pinching cell respective the second pinching cell is less than a degree of rotation of the second pinching cell respective to the first pinching cell.

14. The clot removal device of claim 12, wherein a degree of rotation of the third pinching cell respective the second pinching cell is greater than a degree of rotation of the second pinching cell respective to the first pinching cell.

15. The clot removal device of claim 1, wherein the first pinching cell is connected to the distal end of the elongated member such that the first pinching cell is rotatable respective the elongated member.

16. The clot removal device of claim 1, wherein the plurality of pinching cells has three or fewer pinching cells in a chain of pinching cells.

17. The clot removal device of claim 16, wherein the plurality of pinching cells has two pinching cells in the chain of pinching cells.

18. A clot removal device for removing a clot from a body vessel, the clot removal device comprising:
- an elongated member sized to traverse vasculature and having a proximal end and a distal end, the elongated member defining a longitudinal axis; and
- an engagement structure connected to the distal end of the elongated member, the engagement structure comprising at least two pinching cells configured to engage the clot in an expanded deployed configuration and to pinch the clot upon actuation to a clot pinching configuration;
- wherein the at least two pinching cells are connected to the elongated member such that each of the at least two pinching cells is rotatable respective to the elongated member substantially about the longitudinal axis, and
- wherein the at least two pinching cells comprise alternating collar pinching cells and joiner pinching cells, the collar pinching cells comprising collars on a first end and a second end of the collar pinching cells, and the joiner pinching cells comprising mating connectors configured to rotatably connect with the collars on a first end and a second end of the joiner pinching cells.

19. A method for manufacturing a clot removal device, the method comprising:
- forming an engagement structure comprising a plurality of pinching cells, wherein each of the plurality of pinching cells comprising connection means to rotatably connect to at least one other pinching cell of the plurality of pinching cells;
- connecting the engagement structure to a distal end of an elongated member sized to transverse the vasculature, the elongated member defining a longitudinal axis; and
- connecting a second pinching cell of the plurality of pinching cells to a first pinching cell via the respective connection means of the first pinching cell and the second pinching cell such that the second pinching cell is rotatable respective to the first pinching cell substantially about the longitudinal axis;
- wherein the plurality of pinching cells comprise alternating collar pinching cells and joiner pinching cells, the collar pinching cells comprising collars on a first end and a second end of the collar pinching cells, and the joiner pinching cells comprising mating connectors configured to rotatably connect with the collars on a first end and a second end of the joiner pinching cells;
- wherein the plurality of pinching cells are configured to engage the clot in an expanded deployed configuration and to pinch the clot upon actuation to a clot pinching configuration.

* * * * *